(12) United States Patent
Murphy et al.

(10) Patent No.: US 11,013,403 B2
(45) Date of Patent: May 25, 2021

(54) METHODS OF DIAGNOSING DISEASES OF MUCOSAL SURFACES

(71) Applicants: The Regents of the University of California, Oakland, CA (US); Wisconsin Alumni Research Foundation, Madison, WI (US)

(72) Inventors: Christopher J. Murphy, Davis, CA (US); Bernardo Yañez-Soto, San Luis Potosi (MX); Vijay Krishna Raghunathan, Houston, TX (US); Nicholas L. Abbott, Madison, WI (US)

(73) Assignees: The Regents of the University of California, Oakland, CA (US); Wisconsin Alumni Research Foundation, Madison, WI (US)

( * ) Notice: Subject to any disclaimer, the term of this patent is extended or adjusted under 35 U.S.C. 154(b) by 327 days.

(21) Appl. No.: 15/763,113

(22) PCT Filed: Sep. 27, 2016

(86) PCT No.: PCT/US2016/053930
§ 371 (c)(1),
(2) Date: Mar. 25, 2018

(87) PCT Pub. No.: WO2017/058774
PCT Pub. Date: Apr. 6, 2017

(65) Prior Publication Data
US 2019/0053702 A1    Feb. 21, 2019

Related U.S. Application Data

(60) Provisional application No. 62/234,290, filed on Sep. 29, 2015.

(51) Int. Cl.
*A61B 3/107* (2006.01)
*A61B 3/10* (2006.01)
(Continued)

(52) U.S. Cl.
CPC .............. *A61B 3/107* (2013.01); *A61B 3/101* (2013.01); *A61B 3/145* (2013.01); *A61B 5/1071* (2013.01);
(Continued)

(58) Field of Classification Search
None
See application file for complete search history.

(56) References Cited

U.S. PATENT DOCUMENTS 8,614,178 B2 * 12/2013 Theisinger .............. A61P 27/02
514/1.1
2013/0053794 A1    2/2013 Cadden et al.
(Continued)

OTHER PUBLICATIONS

Fischer Scientific, "Material Safety Data Sheet Phosphate Buffered Saline Solution", https://fscimage.fishersci.com/msds/91348.htm (Year: 2008).*
(Continued)

*Primary Examiner* — Jason M Sims
*Assistant Examiner* — James Stewart Stambaugh, III
(74) *Attorney, Agent, or Firm* — Casimir Jones S.C.; J. Mitchell Jones

(57) ABSTRACT

Provided are methods for assessment of surface rugosity of a layer of live cells using tools that determine contact angle and contact angle hysteresis.

26 Claims, 18 Drawing Sheets

(51) Int. Cl.
*A61F 9/007* (2006.01)
*A61B 3/14* (2006.01)
*A61B 5/107* (2006.01)
*G01N 13/02* (2006.01)

(52) U.S. Cl.
CPC .. *A61F 9/00736* (2013.01); *G01N 2013/0208* (2013.01)

(56) References Cited

U.S. PATENT DOCUMENTS

2013/0274691 A1 10/2013 De Juan, Jr. et al.
2014/0221941 A1 8/2014 Erickson et al.

OTHER PUBLICATIONS

Yañez-Soto, B., Mannis, M. J., Schwab, I. R., Li, J. Y., Leonard, B. C., Abbott, N. L., & Murphy, C. J. (2014). Interfacial Phenomena and the Ocular Surface. The Ocular Surface, 12(3), 178-201. doi: 10.1016/j.jtos.2014.01.004 (Year: 2014).*
International Search Report, International Patent Application No. PCT/US2016/053930, dated Feb. 7, 2017, 4 pages.

* cited by examiner

Fig. 1A-C

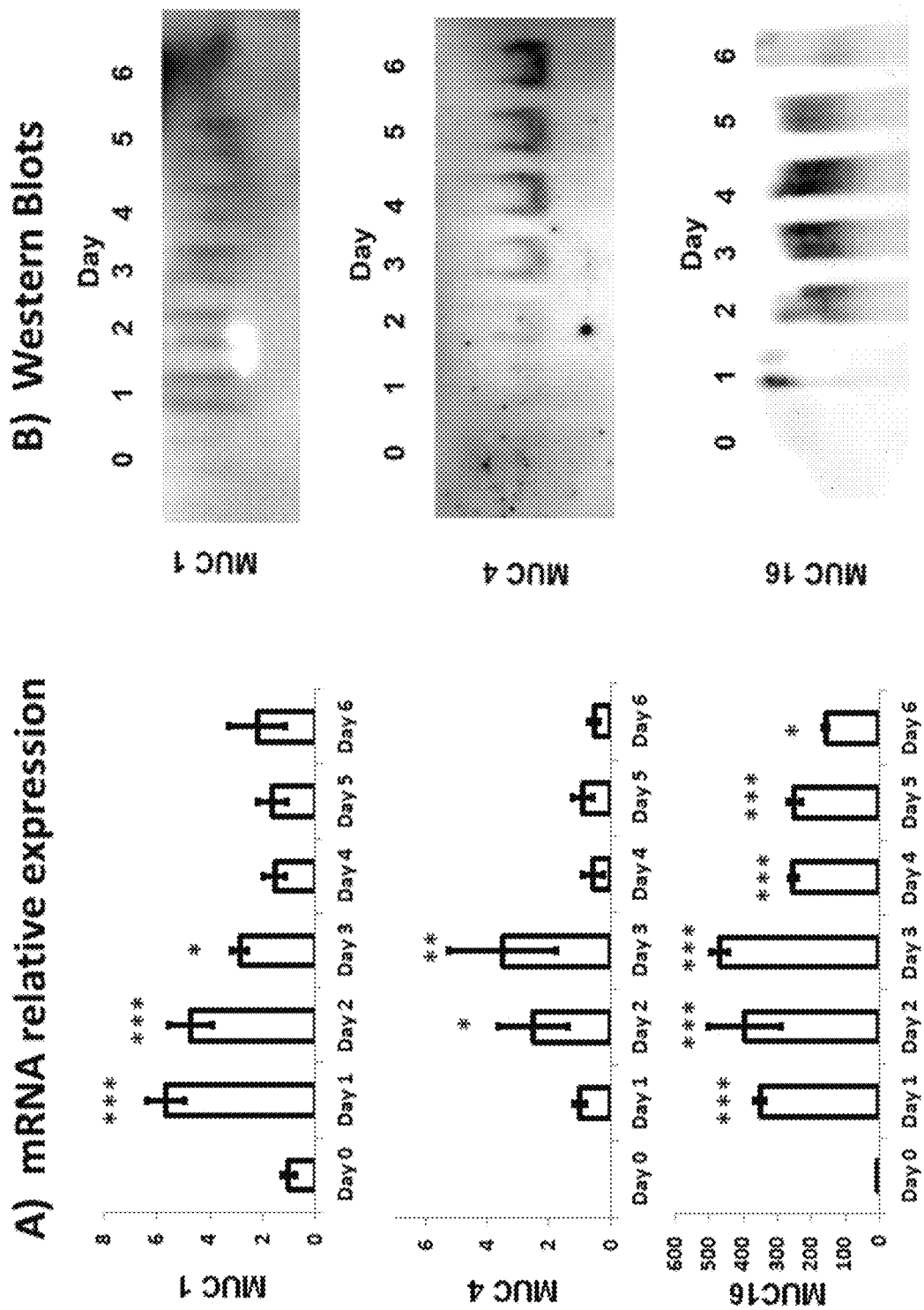
Fig. 4A-B

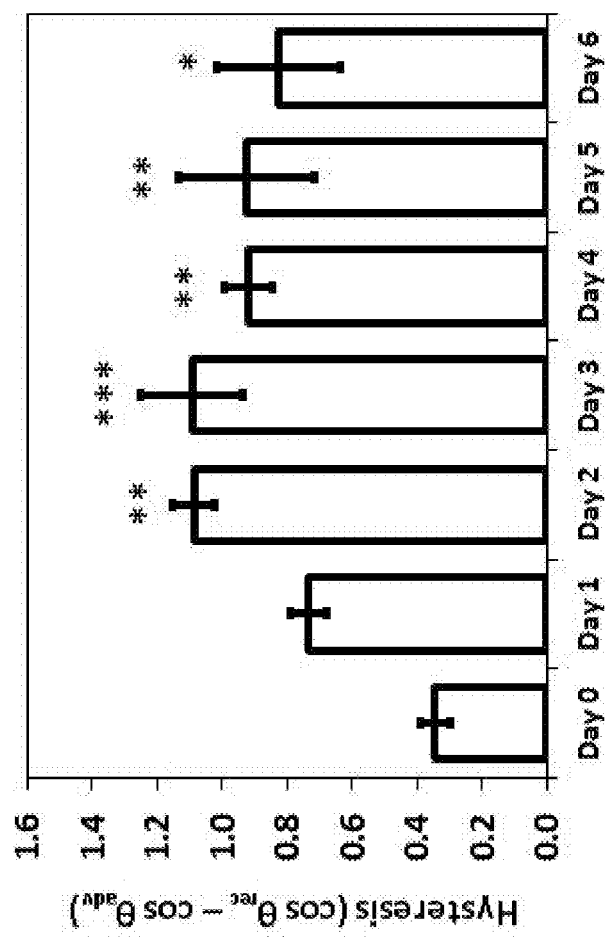
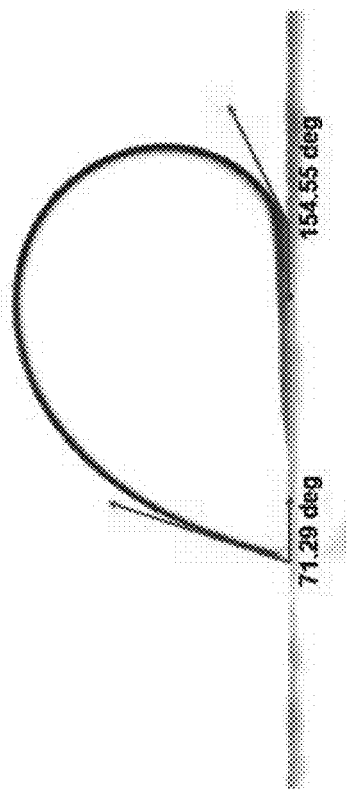
*Fig. 5A-B*

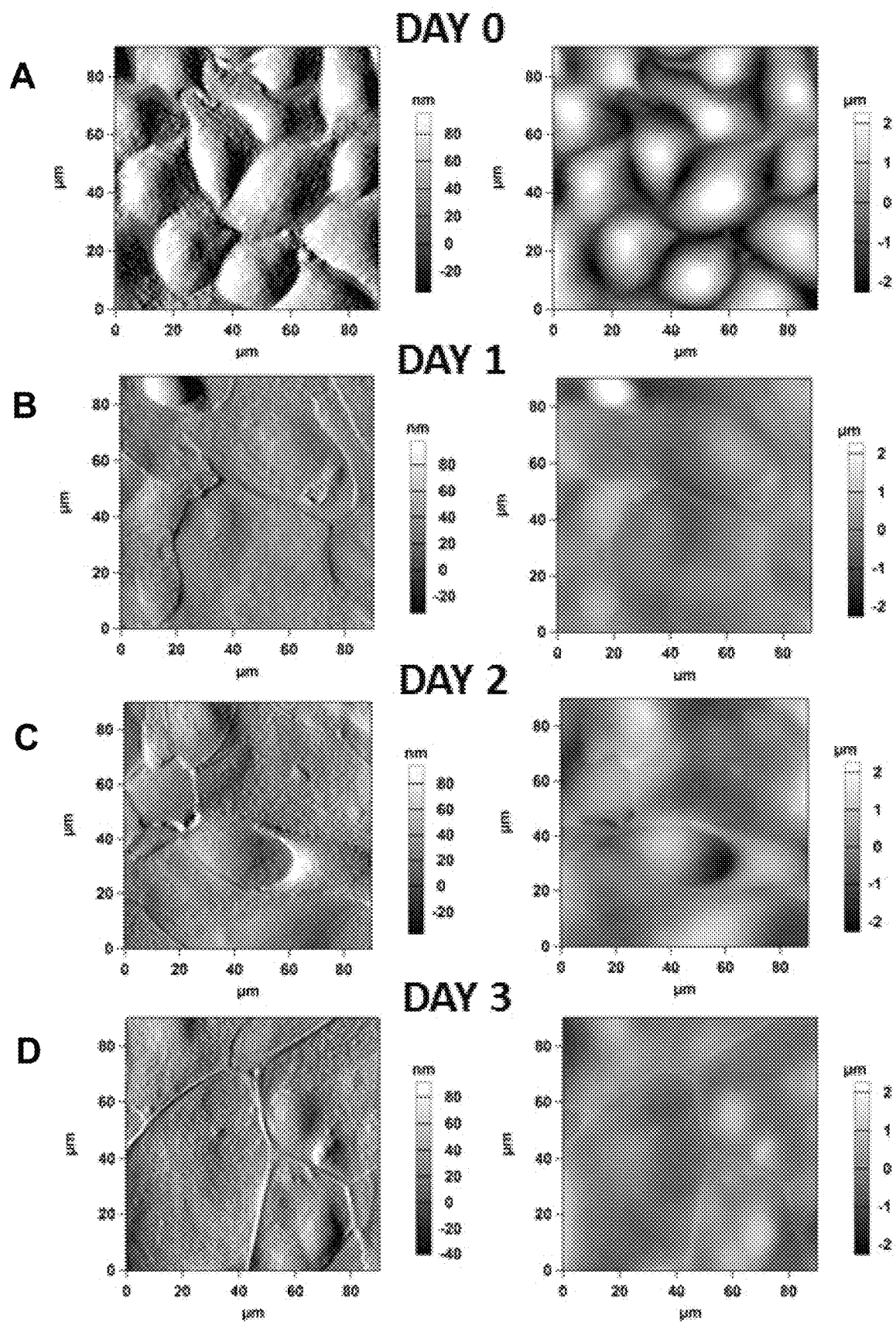
Fig. 7A-D

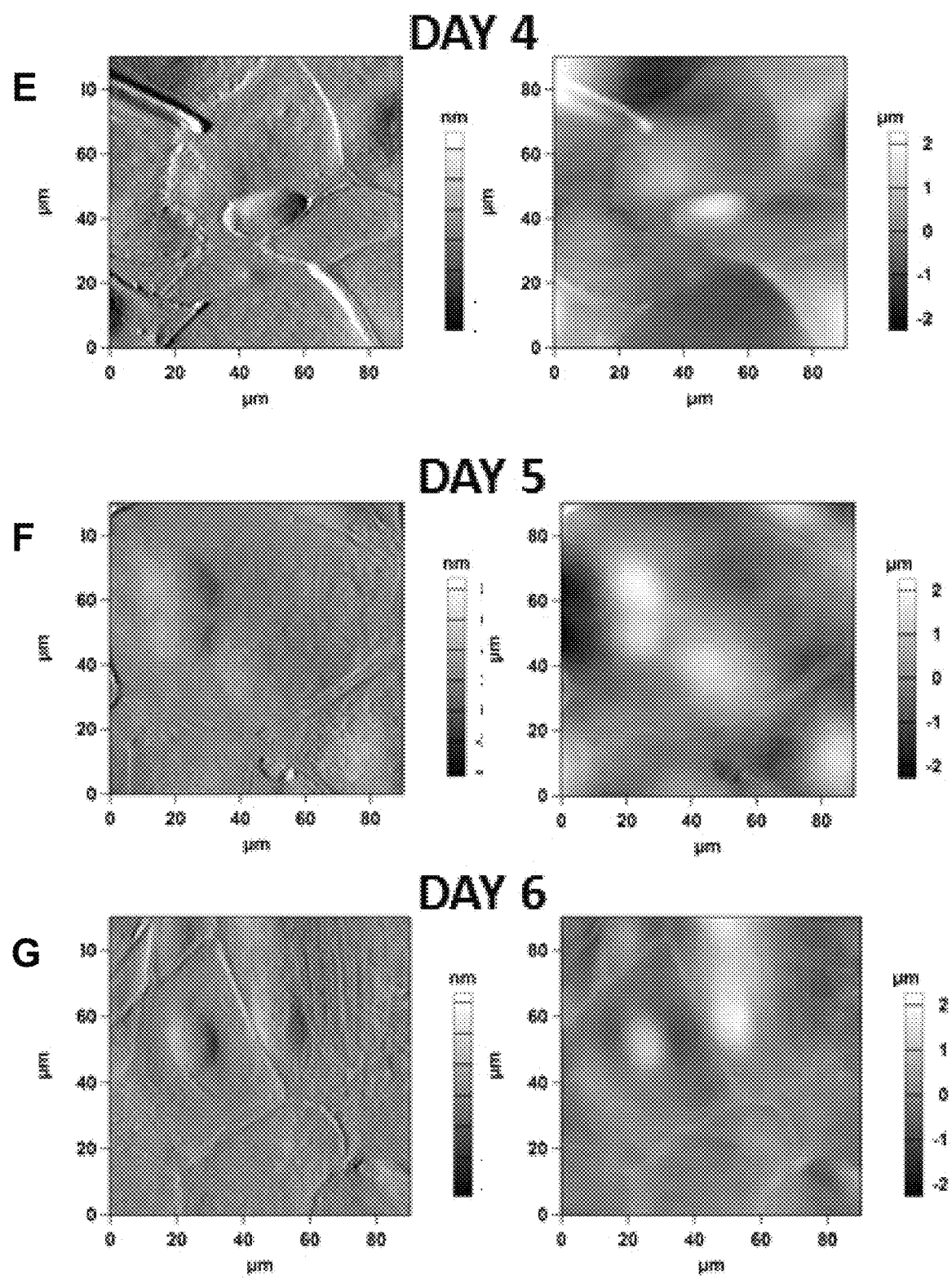
Fig. 7E-G

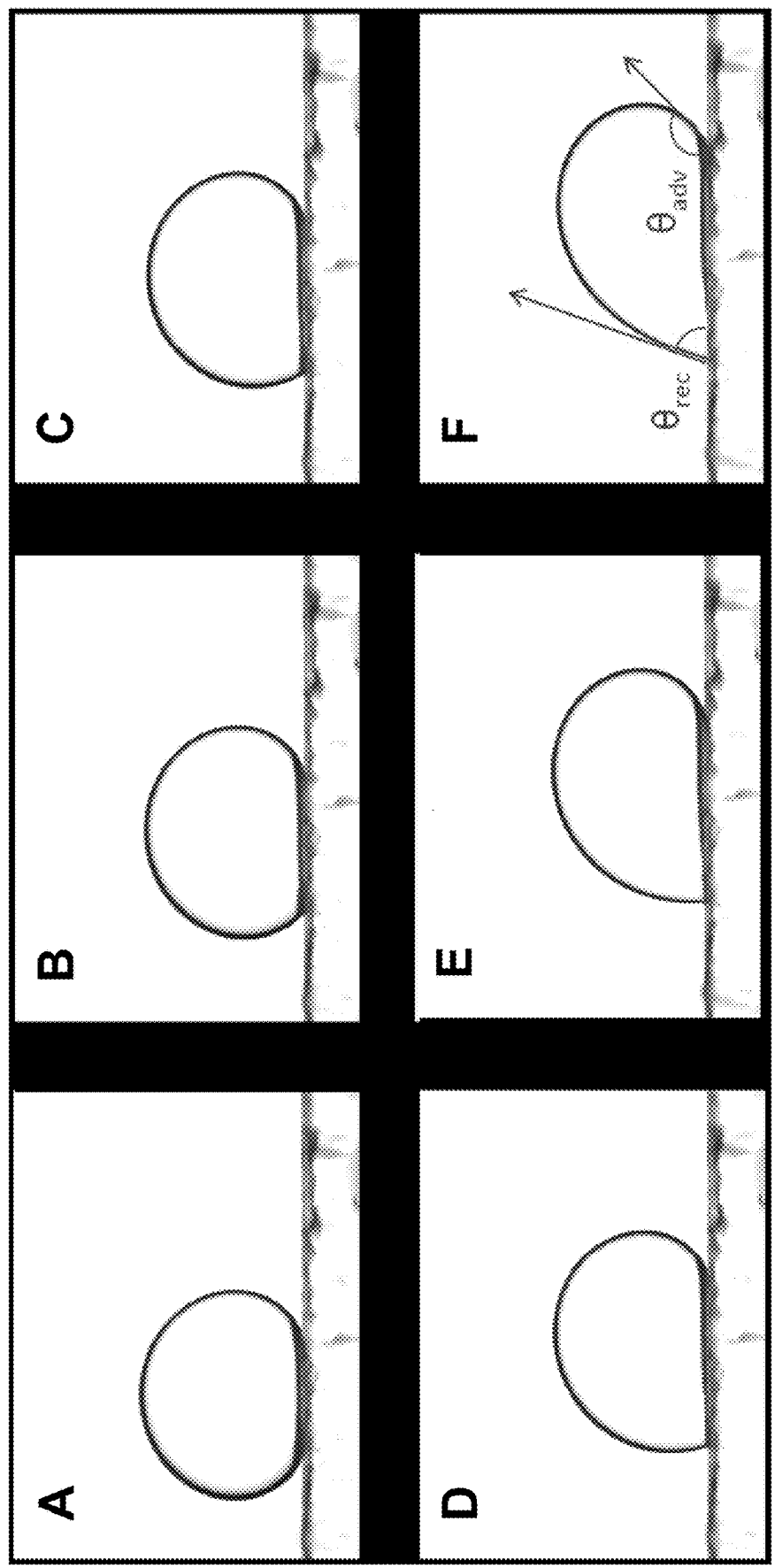
Fig. 12A-F

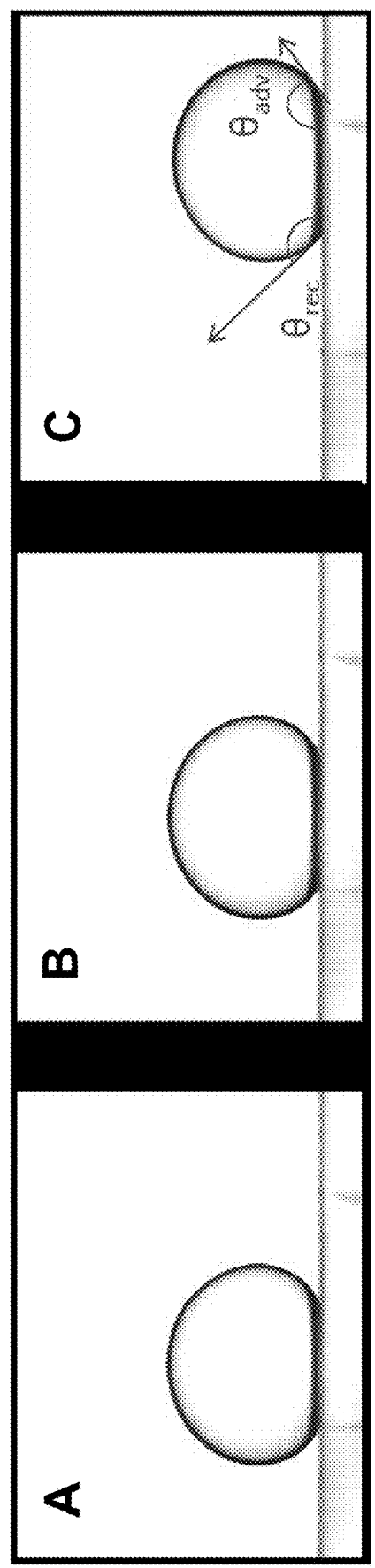
Fig. 13A-C

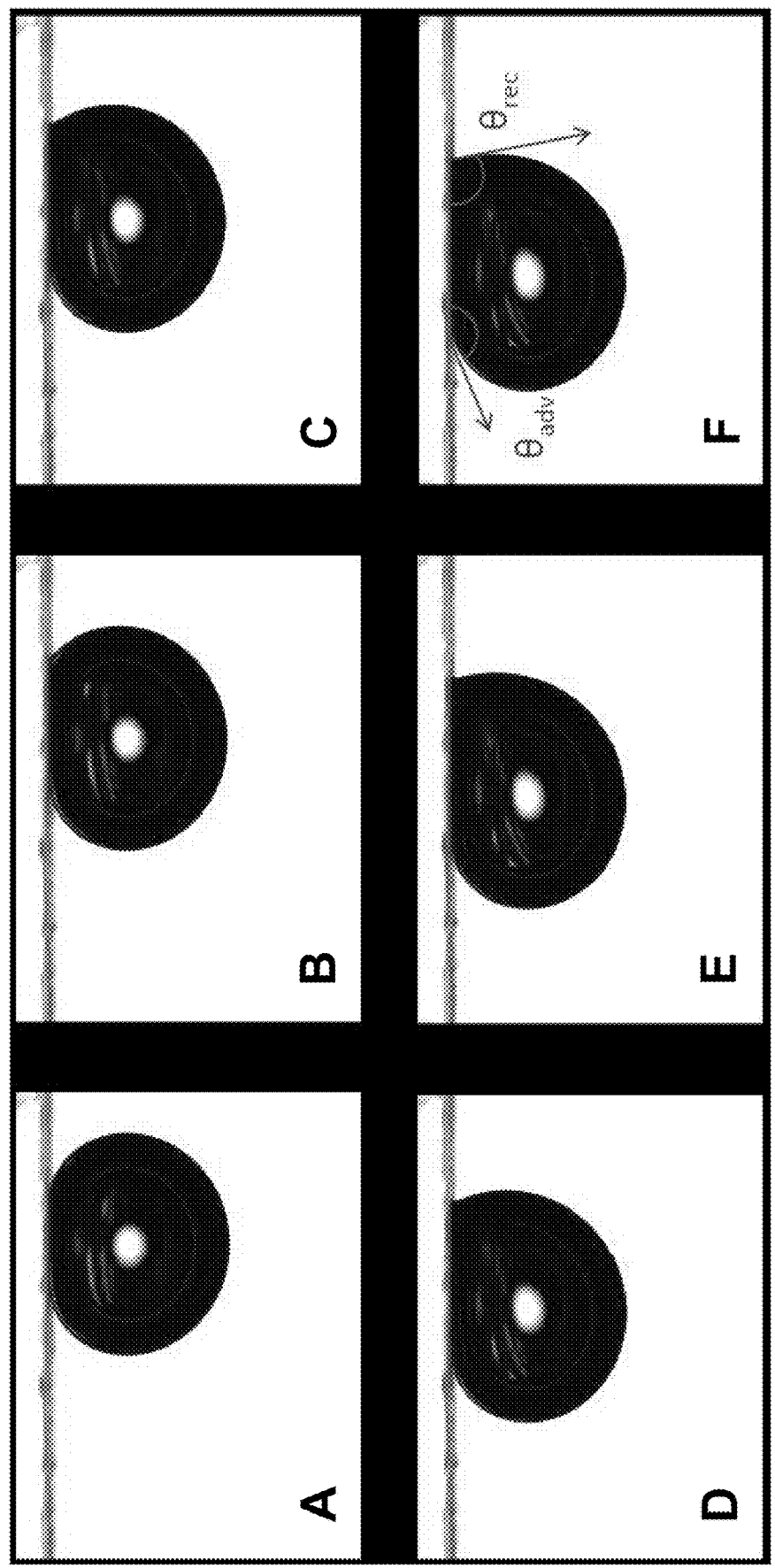
Fig. 14A-F

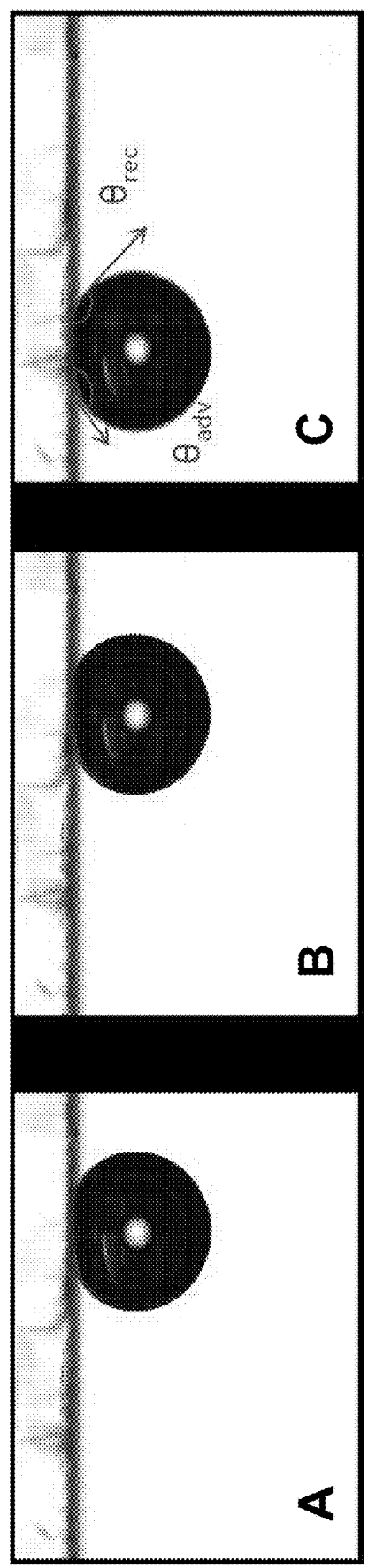
Fig. 15A-C

METHODS OF DIAGNOSING DISEASES OF MUCOSAL SURFACES

CROSS-REFERENCE TO RELATED APPLICATIONS

This application is a U.S. National Phase under 35 U.S.C. § 371 of Intl. Appl. No. PCT/US2016/053930, filed on Sep. 27, 2016, which claims the benefit under 35 U.S.C. § 119(e) of U.S. Provisional Application No. 62/234,290, filed on Sep. 29, 2015, which are hereby incorporated herein by reference in their entireties for all purposes.

FIELD

Provided are methods for assessment of surface rugosity of a layer of live cells using tools that determine contact angle and contact angle hysteresis.

BACKGROUND

Dry eye syndrome is a multifactorial disease of the ocular surface with clinical findings including discomfort, visual disturbance and tear film instability (1). In the US, it is estimated that 7.8% of women age 50 and over (2) and 4.34% of men age 50 and over (3) are affected by dry eye syndrome. Although the International Dry Eye WorkShop (DEWS) has categorized the types of dry eye as 1) aqueous-deficient and 2) evaporative (1), dry eye syndrome and other ocular surface disorders also involve the interaction between the cellular surface of the eye and the liquid film constituted by the tears (4).

It is widely believed that the stability/instability of the tear film depends on the surface properties of the epithelial surface, especially its wettability, or degree of retention of the tear film in contact with the ocular surface (5-7). While the wetting properties have traditionally been attributed to the presence of a hydrophilic glycocalyx (8), specifically to the highly O-glycosylated membrane-associated mucins of the ocular surface (principally MUC1, MUC4 and MUC16) (9), to our knowledge, there are no studies that directly correlate the expression and spatial distribution of cell associated mucins to the physicochemical surface properties of the ocular surface.

Immortalized corneal epithelial cell lines have been reported to differentiate, stratify and express significant amounts of mucins when cultured as a confluent monolayer of cells and stimulated with 10% fetal bovine serum (FBS) and 10 ng/mL of epithelial growth factor (EGF) (10). In this work we induced stratification of an hTERT immortalized corneal epithelial (hTCEpi) cell line (11) over a period of 6 days and characterized the expression of mucins to correlate with the surface properties of the cells.

One method to evaluate surface properties is the sessile drop contact angle technique (5-7,12). This method is widely used and performed by measuring the contact angle between a liquid drop and a solid in air. However, measurements of the contact angle of water drops on cell cultures or tissues are misleading, because the thin film of liquid covering the surface on hydrated cells impedes the measurement of an angle. Furthermore, if the cell surface is allowed to dry, the contact angle changes values, dependent of the moisture level, as observed by Tiffany (7), suggesting the loss of the native state of the cell surface. To overcome some of the challenges intrinsic to using water as the probe, other liquids can be used to characterize surfaces, such as polar liquids (e. g. glycerol or formamide), or non-polar lipids (e.g. diiodomethane or benzene). However, polar liquids can disturb the cells due to the difference in osmolarity between the liquid and the cytosol, while many non-polar liquids interact with the phospholipids of the cellular membrane, disrupting it (13). Therefore fluid(s) used to measure contact angles of cell surfaces bathed in a fluid environment influence the interfacial properties.

Dry eye diseases and disorders are diagnosed using a battery of tests, including questionnaires, ocular surface staining, indirect measurement of the tear volume, determining the stability of tear film (tear film break up time), quantifying osmolality of the tears, and a variety of biomarkers. Although many of these endpoints provide information of certain attributes, they do not provide a definitive assessment of the state of the ocular surface, and none of these tests describes the dynamic interdependence of the constituents of the tear film and the interaction with the cellular constituents of the ocular surface.

SUMMARY

In one aspect, provided is a device to measure contact angle and contact angle hysteresis on a surface or layer of live/viable cells. In some embodiments, the device comprises:

i) a hollow outer cylinder comprised of a transparent material comprising a top end and a bottom end, the top end comprising an aperture of a diameter sufficient to allow passage of a syringe; the bottom end configured to form a liquid impermeable seal between an inner space of the cylinder and the surface of the eye of a mammal;

ii) a syringe comprising an inner cylinder and plunger, the syringe positioned along the center axis of the cylinder, wherein the plunger dispenses fluid into the inner space of the hollow outer cylinder near the bottom end. In varying embodiments, the hollow outer cylinder contains a first fluid that is isotonic to the cells of the eye (e.g., corneal epithelium). In varying embodiments, the fluid that is isotonic to the cells of the eye (e.g., corneal epithelium) is transparent. In varying embodiments, the fluid that is isotonic to the cells of the eye (e.g., corneal epithelium) is colorless. In varying embodiments, the fluid that is isotonic to the cells of the eye (e.g., corneal epithelium) is selected from saline solution or artificial tears. In varying embodiments, the hollow outer cylinder is comprised of a material selected from the group consisting of glass, quartz or polymethylmethacrylate (PMMA). In varying embodiments, the hollow outer cylinder comprises an inner diameter in the range of about 10-15 mm, e.g., about 10 mm, 10.5 mm, 11 mm, 11.5 mm, 12 mm, 12.5 mm, 13 mm, 13.5 mm, 14 mm, 14.5 mm or 15 mm. In varying embodiments, the bottom end of the hollow outer cylinder is configured to form a liquid impermeable seal between an inner space of the cylinder and the surface of the cornea of the mammal. In varying embodiments, the aperture is centered in the top end of the hollow outer cylinder. In varying embodiments, the syringe comprises an outer diameter in the range of about 3-10 mm. In varying embodiments, the syringe comprises a blunt end or blunt-tipped needle. In varying embodiments, the needle comprises a gauge in the range of 22-28 (outer diameter (OD) 0.72-0.36 mm and ID 0.41-0.18 mm), e.g., 22 gauge (OD 0.72 mm), 22s gauge (OD 0.72 mm), 23 gauge (OD 0.64 mm), 24 gauge (OD 0.57 mm), 25 gauge (OD 0.51 mm), 26 gauge (OD 0.46 mm), 26s gauge (OD 0.47 mm), 27 gauge (OD 0.41 mm), or 28 gauge (OD 0.36 mm). In varying embodiments, the bottom end of the hollow outer cylinder comprises a cuff or ring or skirt comprised of a flexible and/or form-fitting material. In varying embodiments, the syringe contains a second fluid, wherein the second fluid is immiscible with the first fluid and comprises a higher density than the first fluid. In varying embodiments, the syringe contains a second fluid selected from the group consisting of a perfluorocarbon and a silicon oil. In varying embodiments, the perfluorocarbon is selected from the group consisting of perfluorodecalin, perfluorooctane and tetradecafluorohexane. In varying embodiments, the mammal is selected from a human, a canine and a feline. In varying embodiments, the device is as depicted in FIG. 8.

In another aspect, provided is a system comprising a device as described above and herein and a camara positioned and focused to obtain images of the surface of the eye sealed within the hollow outer cylinder. In varying embodiments, the camera is in communication with the device. In varying embodiments, the plunger of the syringe of the device is in communication with a regulator that depresses and retracts/pulls up the plunger in an automated and/or remotely controlled manner. In varying embodiments, the plunger of the syringe of the device is in communication with a microsyringe pump that depresses and retracts/pulls up the plunger in an automated and/or remotely controlled manner.

In a further aspect, provided is a method of determining the ability of a corneal surface of a subject to retain moisture (e.g., the wettability of the surface). In some embodiments, the methods comprise:

a) contacting the corneal surface of the subject with a device as described above and herein;

b) dispensing one or more drops of the second fluid into the first fluid such that the drops of the second fluid contact the corneal surface of the subject;

c) measuring at several points of contact (i) the advancing contact angle, and (ii) the receding contact angle of the drops of the second fluid in contact with the corneal surface;

d) calculating the contact angle hysteresis of the combined measurements of the several points of contact, wherein a contact angle hysteresis value at or above a threshold value indicates a normal or sufficient ability of the corneal surface to retain moisture, and a contact angle hysteresis value below the threshold value indicates an abnormal or deficient ability of the corneal surface to retain moisture (e.g., indicative of a dry eye disorder). In varying embodiments, the method further comprises moving the device to a second or subsequent point of contact on the corneal surface and repeating steps b) to d). In varying embodiments, the one or more drops comprise an average diameter of about 1-5 mm, e.g., about 1 mm, 1.5 mm, 2.0 mm, 2.5 mm, 3.0 mm, 3.5 mm, 4.0 mm, 4.5 mm, 5.0 mm. In varying embodiments, the methods further comprise measuring the static contact angle. In varying embodiments, the measuring step is performed by obtaining a collection of digital images of the drops of the second fluid in contact with the corneal surface. In varying embodiments, the advancing contact angle values are measured at predetermined time increments (e.g., every 2.0 sec, 1.5 sec, 1.0 sec, 0.5 sec) while the contact point of the drop advances across the corneal surface. In varying embodiments, the receding contact angle values are measured at predetermined time increments (e.g., every 2.0 sec, 1.5 sec, 1.0 sec, 0.5 sec) while the contact point of the drop recedes across the corneal surface. In varying embodiments, the contact angle hysteresis value of the average advancing contact angle and the average receding contact angle from the combined measurements of the several points of contact is calculated by applying the equation: cosine of the average receding contact angle minus the cosine of the average advancing contact angle (cos $\theta_{rec}$–cos $\theta_{adv}$). In varying embodiments, the threshold value is in the range of about 0.6 to about 1.0, e.g., about 0.7 to 0.9, e.g., about 0.60. 0.61, 0.62, 0.63, 0.64, 0.65, 0.66, 0.67, 0.68, 0.69, 0.70. 0.71, 0.72, 0.73, 0.74, 0.75, 0.76, 0.77, 0.78, 0.79, 0.80. 0.81, 0.82, 0.83, 0.84, 0.85, 0.86, 0.87, 0.88, 0.89, 0.90, 0.91, 0.92, 0.93, 0.94, 0.95, 0.96, 0.97, 0.98, 0.99 or 1.0.

In a further aspect, provided is a method of determining the contact angle hysteresis on a surface or layer of live/viable cells. In varying embodiments, the method comprises:

a) immersing a layer of live or viable cells attached to a support substrate in a reservoir comprising a solution that is isotonic to mammalian cells, wherein the support substrate is positioned at or near the bottom of the reservoir and the layer of cells is above the support substrate;

b) introducing into the solution one or more drops of a second solution that is immiscible with the isotonic solution, wherein the drops contact the layer of cells;

c) measuring at several points of contact (i) the advancing contact angle, and (ii) the receding contact angle of the drops of the second solution in contact with the layer of cells;

d) calculating the contact angle hysteresis of the combined measurements of the several points of contact. In some embodiments, the second solution is selected from the group consisting of a perfluorocarbon and a silicon oil. In some embodiments, the perfluorocarbon is selected from the group consisting of perfluorodecalin, perfluorooctane and tetradecafluorohexane.

In a related aspect, provided is a method of determining the contact angle hysteresis on a surface or layer of live/viable cells. In some embodiments, the method comprises:

a) immersing a layer of live or viable cells attached to a support substrate in a transparent reservoir comprising an solution that is isotonic to mammalian cells, wherein the support substrate is inverted and positioned at or near the top of the reservoir, and the layer of cells is below the support substrate;

b) introducing into the solution one or more air or gas bubbles, wherein the bubbles contact the layer of cells;

c) measuring at several points of contact (i) the advancing contact angle, and (ii) the receding contact angle of the bubbles in contact with the layer of cells;

d) calculating the contact angle hysteresis of the combined measurements of the several points of contact.

With respect to embodiments of the methods for determining the contact angle hysteresis on a surface or layer of live/viable cells, in varying embodiments, the method maintains hydration of the cell surface and/or avoids disruption of the chemical components of the cellular membrane. In varying embodiments, the cells are mammalian corneal cells. In varying embodiments, the mammalian corneal cells are selected from human, canine and feline corneal cells. In varying embodiments, the solution that is isotonic to a mammalian cell is transparent. In varying embodiments, the solution that is isotonic to a mammalian cell is colorless. In varying embodiments, the solution that is isotonic a mammalian cell is a saline solution, e.g., phosphate buffered saline (PBS). In varying embodiments, the support substrate is comprised of a material selected from the group consisting of glass, silicon, polystyrene, or any other tissue culture material. In varying embodiments, the several points of contact cover substantially the entirety of the layer of cells attached to the support substrate. In varying embodiments, the one or more drops or bubbles comprise an average diameter of about 1-5 mm, e.g., about 1 mm, 1.5 mm, 2.0 mm, 2.5 mm, 3.0 mm, 3.5 mm, 4.0 mm, 4.5 mm, 5.0 mm. In varying embodiments, the methods further comprise measuring the static contact angle. In varying embodiments, the measuring step is performed by obtaining a collection of digital images of the drops or bubbles in contact with the layer of cells. In varying embodiments, the advancing contact angle values are measured at predetermined time increments (e.g., every 2.0 sec, 1.5 sec, 1.0 sec, 0.5 sec) while the contact point of the drops or bubbles advances across the layer of cells. In varying embodiments, the receding contact angle values are measured at predetermined time increments (e.g., every 2.0 sec, 1.5 sec, 1.0 sec, 0.5 sec) while the contact point of the drops or bubbles recedes across the layer of cells. In varying embodiments, the support substrate is tilted to adjust the rate that the drops or bubbles move across the layer of cells. In varying embodiments, the contact angle hysteresis value of the average advancing contact angle and the average receding contact angle from the combined measurements of the several points of contact is calculated by applying the equation: cosine of the average receding contact angle minus the cosine of the average advancing contact angle ($\cos \theta_{rec} - \cos \theta_{adv}$).

In a further aspect, provided are kits comprising one or more devices, as described above and herein. In varying embodiments, the kits comprise multiple hollow outer cylinders of varying diameters, heights and geometries at the bottom end. In varying embodiments, the kits comprise a system as described above and herein.

Definitions

The term "contact angle hysteresis" refers to the difference in contact angle when a drop or bubble is advancing (advancing contact angle) versus when it is retreating (receding contact angle) on a heterogeneous surface.

The term "transparent" refers to sufficient transparency of a solution and fluid barrier structure (e.g., reservoir, wall of hollow outer cylinder) such that images of sufficient resolution for determining the contact angles (static, advancing and receding) of a drop or bubble in contact with a layer of cells can be obtained. Quantitatively, sufficiently transparency refers to transmittance of light through the solution and fluid barrier structure such that at least of 25% (one quarter) of the used light is able to pass through the solution and fluid barrier structure without scattering.

The terms "individual," "patient,", "subject" interchangeably refer to a mammal, for example, a human, a non-human primate, a domesticated mammal (e.g., a canine or a feline), an agricultural mammal (e.g., equine, bovine, ovine, porcine), or a laboratory mammal (e.g., rabbit).

The term "dry eye diseases" refers to a group of conditions each characterized by decreased tear production or increased tear film evaporation. See, e.g., *Ocul Surf* (2007) 5(2):75-92; Latkany, *Curr Opin Ophthalmol.* (2008) 19(4): 287-91.

"Keratoconjunctivitis sicca (KCS)," "keratitis sicca," "xerophthalmia," or "dry eye syndrome (DES)" is a dry eye disease caused by either decreased tear production or increased tear film evaporation. Keratoconjunctivitis sicca is usually due to inadequate tear production. The aqueous tear layer is affected, resulting in aqueous tear deficiency (ATD) or lacrimal hyposecretion. In subjects with KCS, the lacrimal gland does not produce sufficient tears to keep the entire conjunctiva and cornea covered by a complete layer. Symptoms include eye irritation (e.g., dryness, burning, sandy-gritty sensations, itching, stinging, fatigue, pain, redness, pulling sensations), stingy discharge from the eyes, and the production of non-lubricating tears. In advanced cases, the epithelium, e.g., of the upper eyelid may undergo squamous metaplasia and loss of goblet cells. Some severe cases may result in thickening of the corneal surface, corneal erosion, punctate keratopathy, epithelial defects, corneal ulceration (sterile and infected), corneal neovascularization, corneal scarring, corneal thinning, and/or even corneal perforation.

Meibomian Gland Dysfunction (MGD) refers to a chronic, diffuse abnormality of the meibomian glands, commonly characterized by terminal duct obstruction and/or qualitative/quantitative changes in the glandular secretion. MGD may result in alteration of the tear film, symptoms of eye irritation, clinically apparent inflammation, and ocular surface disease. Nichols, et al., *Investigative Ophthalmology & Visual Science* (2011) 52(4):1922-1929. MGD is considered an "evaporative" dry eye condition, oftentimes due to a loss of amount and/or integrity of the lipid component of the precorneal tear film. MGD conditions include without limitation posterior blepharitis, meibomian gland disease, meibomitis, meibomianitis, and meibomian keratoconjunctivitis. The pathophysiological mechanisms can be broadly categorized into 1. low delivery of meibum (due to obstruction or hyposecretion—either primary of secondary in nature) and 2. high delivery of meibum (either primary or secondary hypersecretion). See, e.g., Nichols, et al., supra; Geerling, et al., *Investigative Ophthalmology & Visual Science* (2011) 52(4):2050-2064; and Nichols, *Investigative Ophthalmology & Visual Science* (2011) 52(4):1917-1921.

BRIEF DESCRIPTION OF THE DRAWINGS

FIGS. 4A-B. A) Mucin mRNA relative expression for the hTCEpi cell cultures at day 0 (unstratified cells), and days 1-6 during the stratification process. For unstratified cells, the expression of MUC1 is low, and the expression of MUC4 and MUC16 is negligible. The expression of mucin mRNA reaches a peak between day 1 and day 3. (n=3. Error bars: Standard Deviation. Significance with respect to undifferentiated cells: * $0.05 \geq p > 0.01$,  $0.01 \geq p > 0.001$, * $0.001 \geq p$). B) Western blots showing the protein expression of mucins for the hTCEpi cell cultures at day 0 (unstratified cells), and days 1-6 during the stratification process. For unstratified cells, the expression of all mucins is negligible. The protein expression of MUC1 and MUC16 reproduce the observed mRNA expression profile, while the protein expression of MUC4 suggests a monotonic increase during the stratification process.

FIGS. 5A-B. A) Contact angle hysteresis. The surface is tilted and the advancing (highest) contact angle and the receding (lowest) contact angle are recorded at the point where the drop starts to slide. B) Contact angle hysteresis of perfluorodecalin drops for the cell cultures at day 0 (unstratified) and days 1-6 during the stratification process. The hysteresis reaches a peak between day 2 and 3 and then decreases, similarly to the expression profile of mucins. (n=3. Error bars: Standard Deviation. Significance with respect to undifferentiated cells: * $0.05 \geq p > 0.01$,  $0.01 \geq p > 0.001$, * $0.001 \geq p$).

FIGS. 7A-G illustrate AFM images of the cell cultures at day 0 (unstratified) and days 1-6 during the stratification process. Left figures represent phase images and right figures represent height images. Unstratified cells show cobblestone morphology, and are tall with no discernable cell junctions, resembling basal corneal epithelial cells. Once exposed to SM, cells flatten and develop marked cell junctions. No other noticeable topographic features are observed.

FIGS. 12A-F illustrate still captions of a sessile drop tilting experiment using perfluorodecalin on stratified cultures (day 3). The still captions correspond to A) No tilting, B) 5° tilting, C) 10° tilting, D) 15° tilting, E) 20° tilting and F) 25° tilting.

FIGS. 13A-C illustrate still captions of a sessile drop tilting experiment using perfluorodecalin on unstratified cultures. The still captions correspond to A) No tilting, B) 2° tilting, C) 5° tilting.

FIGS. 14A-F illustrate still captions of a captive bubble (air) experiment on stratified cultures (day 3). The still captions correspond to A) No tilting, B) 5° tilting, C) 10° tilting, D) 15° tilting, E) 20° tilting and F) 25° tilting.

FIGS. 15A-C illustrate still captions of a captive bubble experiment (air) on unstratified cultures. The still captions correspond to A) No tilting, B) 1° tilting, C) 3° tilting.

DETAILED DESCRIPTION

1. Introduction

Dry Eye Diseases (DEDs) are an array of diseases of the ocular surface with symptoms including discomfort, visual disturbance and foreign object sensations. In the US, it is estimated that 7.8% of women and 4.3% of men over 50 years are affected by dry eye. DEDs are one of the top three economically important ocular diseases affecting human patients. DEDs involve the interaction between the ocular surface epithelia and the aqueous tear film. The retention of the tear film on the ocular surface depends on many properties, such as the viscosity of tears, the interblinking period and the molecular interactions between the cellular surface and the tear fluid. One method to evaluate those molecular interactions is the measurement of the contact angle between a drop of liquid or gas and the surface. Generally speaking, the lower the contact angle is, the higher the molecular interactions between the solid and the fluid/gas are. Flat, chemically homogeneous surfaces usually have a unique contact angle for a given liquid/gas; however, heterogeneous surfaces (such as biological surfaces) show a different contact angle when the drop is advancing (advancing contact angle), than when it is retreating (receding contact angle). That difference is known as the contact angle hysteresis, and arises from the "pinning" of the contact line of a drop or bubble on defects and heterogeneities. The contact angle hysteresis is a measurement of the surface heterogeneity and it also correlates to a "retentive force" that stabilizes a fluid on a surface, keeping it from "rolling over." The contact angle hysteresis provides a relevant and distinctive characteristic that facilitates the evaluation and diagnosis of dry eye.

Herein, we describe a diagnostics method for determining ocular surface health that characterizes the surface properties of the corneal epithelium by measuring contact angle and contact angle hysteresis as a means to correlate with the "wettability" of the surface and the heterogeneity of the cellular constituents of the surface. These properties serve a fundamental and important role in the stability and retention of the tear film and, to date, have never been used to diagnose ocular surface pathologies.

Figure 1:
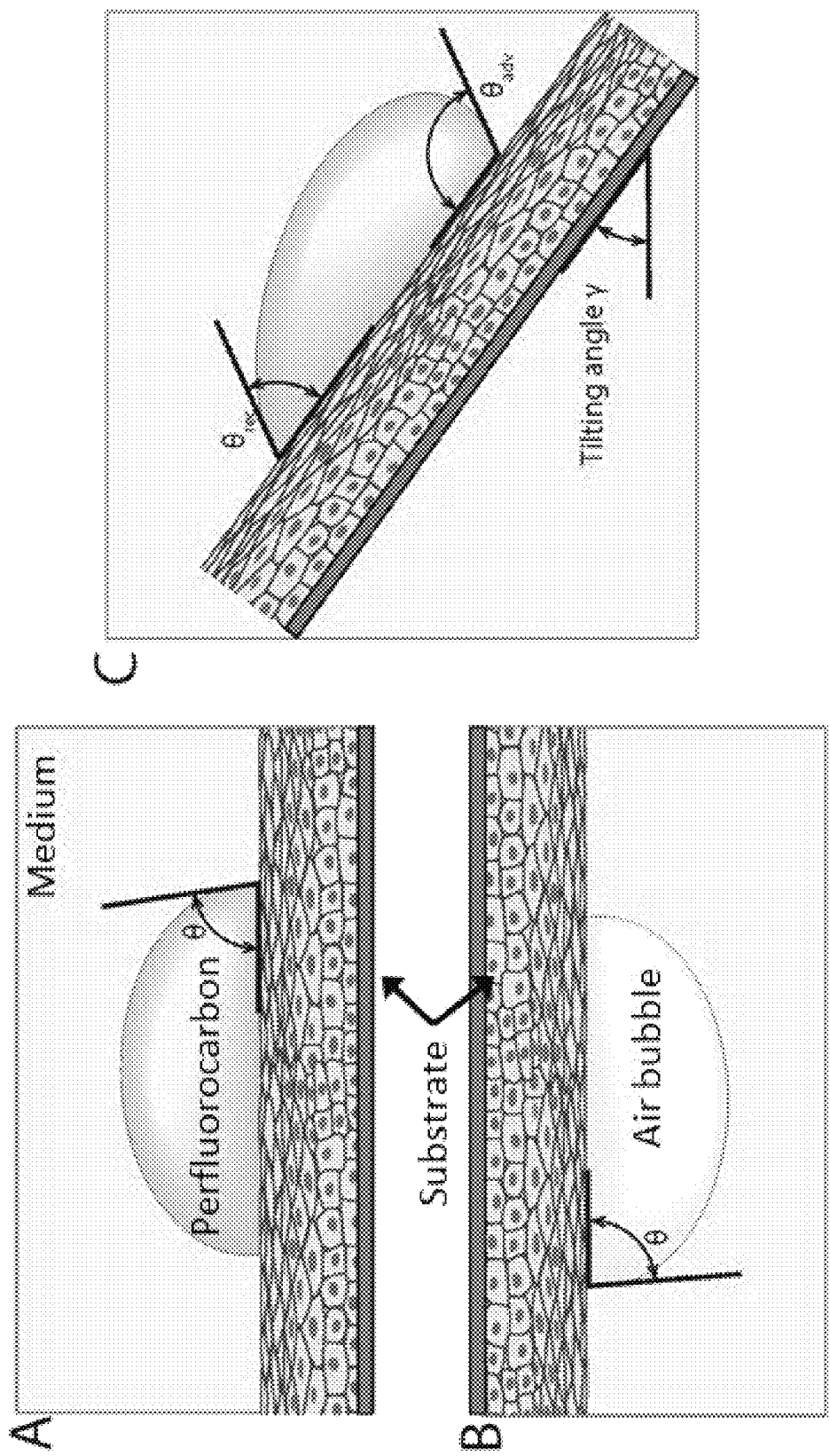
FIGS. 1A-C. A) 2-liquid method to measure contact angle. In this system, the bulk fluid is PBS and the drop is a perfluorocarbon. B) Captive bubble method to measure contact angle. C) Tilting of the apparatus to measure the advancing and the receding contact angle.

The methods described herein are based, in part, on the determination of the influence of mucin expression (e.g., from an immortalized human corneal epithelial cell line (hTCEpi)) on the surface properties of cells, such as wettability, contact angle and surface heterogeneity. We employed the use of a 2-liquid system, where cells were immersed in an isotonic physiologic buffer and the contact angle was recorded using a non-reactive non-polar liquid (perfluorocarbon) deposited on the cell surface (FIG. 1A). We also performed the captive bubble method, where the surface of interest was inverted and an air bubble was trapped in contact with the surface (FIG. 1B). Both methods permit the measurement of the contact angle and the contact angle hysteresis, which is a measurement that correlates to the uniformity of the surface. For smooth and uniform surfaces, drops have unique contact angles. However, on heterogeneous surfaces, such as biological surfaces, drops get pinned by defects, and possess an advancing and a receding angle of contact, which may be recorded by tilting the apparatus (FIG. 1C). The intrinsic biochemical make-up and surface topography of the ocular surface contribute to this heterogeneity, and the extent to which this promotes the retention of the tear film at the ocular surface is understudied. These measurements allow the evaluation of the surface properties at different maturation levels of the glycocalyx during the stratification process of immortalized human corneal epithelial cells.

In demonstrating the operability of the methods, hTCEpi cells were cultured to confluence in serum-free media. The medium was then replaced by stratification medium to induce mucin biosynthesis. The mucin expression profile was analyzed using qPCR and Western blots. Contact angles were measured using a two immiscible-liquids method and contact angle hysteresis was evaluated by tilting the apparatus and recording the advancing and receding contact angles. The spatial distribution of mucins was evaluated with fluorescently labeled lectin.

The results demonstrated that the surface chemical heterogeneity of the corneal epithelium may influence the dynamic behavior of the tear film by "pinning" of the contact line between the cellular surface and the aqueous tear film. Briefly, hTCEpi cells expressed the three main ocular mucins (MUC1, MUC4 and MUC16) with a maximum between days 1 and 3 of the stratification process. Upon stratification, cells caused a very significant increase of the contact angle hysteresis, suggesting the development of spatially discrete and heterogeneously distributed surface features, defined by topography and/or chemical functionality. Although AFM measurements showed no formation of appreciable topographic features on the surface of the cells, we observed a significant increase of the surface chemical heterogeneity.

Figure 8:
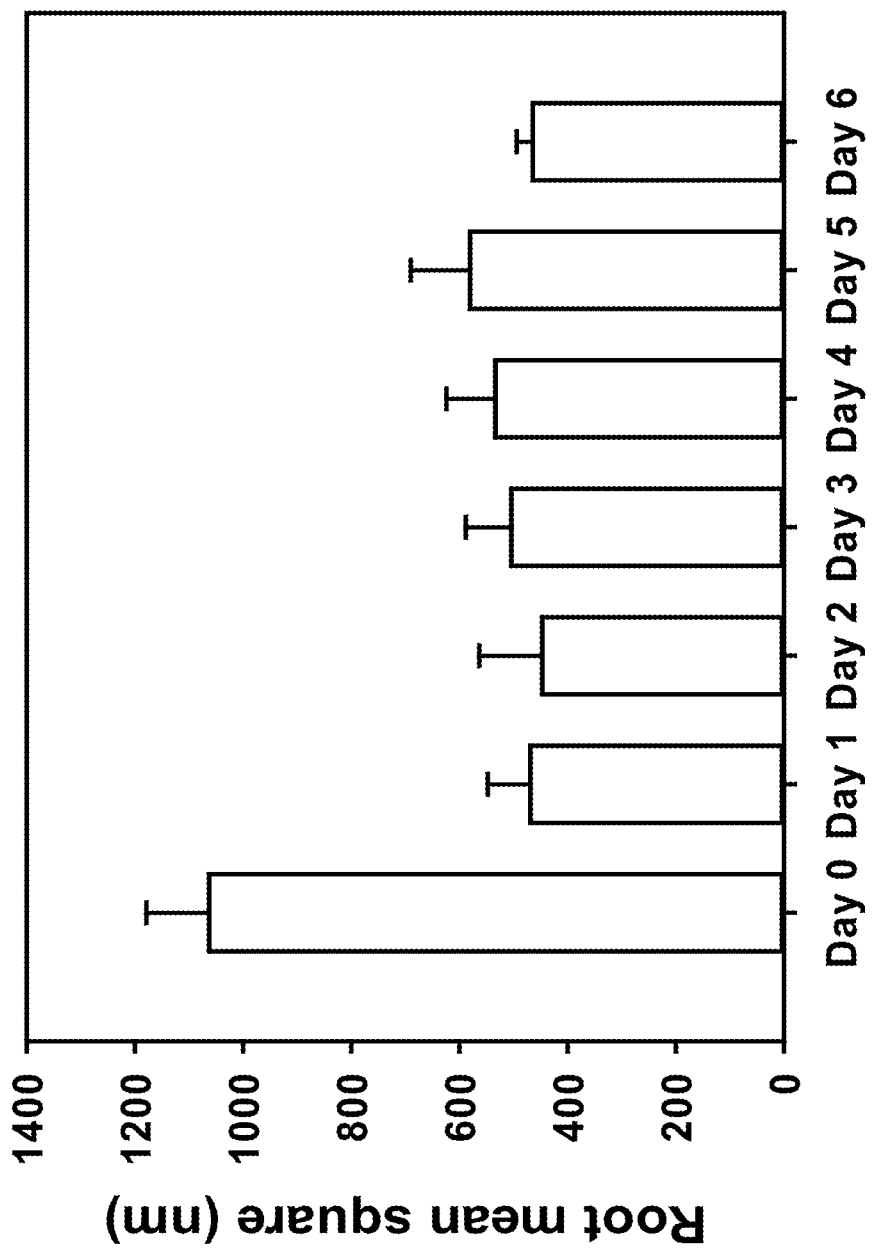
FIG. 8 illustrates root mean square (RMS) obtained from the height trace of AFM.

2. Device for Determining Contact Angle Hysteresis on the Surface of Live Cells In one aspect, provided is a device, useful to measure contact angle and contact angle hysteresis on a surface or layer of live/viable cells, including a surface or layer of cells on a subject. In varying embodiments, the device finds use to measure contact angle and contact angle hysteresis on the ocular surface of patients. The device is used by employing a method whereby a liquid or gas with known biophysical properties is placed in contact with the ocular surface and the contact angle is measured both statically as well as in advancing and receding states. One illustrative embodiment of the structural features of a contemplated device, including as a system in communication with a camera, is depicted in FIG. 8. In use, the device is placed in contact with the surface of live/viable cells, e.g., the ocular surface of a subject; a fluid or gas is placed in contact with the ocular surface and the contact angle—a measure of the interfacial properties of the surface—can be determined through capture of an image or series of images and subsequent quantitative determination of advancing and receding contact angles. These measurements of advancing and receding contact angles describe the surface properties of surface of live cells, e.g., the ocular surface epithelium, and can be used as a diagnostic tool, e.g., for ocular surface diseases, including dry eye syndrome.

In some embodiments, the device comprises:

i) a hollow outer cylinder comprised of a transparent material comprising a top end and a bottom end, the top end comprising an aperture of a diameter sufficient to allow passage of a syringe; the bottom end configured to form a liquid impermeable seal between an inner space of the cylinder and the surface of the eye of a mammal;

ii) a syringe comprising an inner cylinder and plunger, the syringe positioned along the center axis of the cylinder, wherein the plunger dispenses fluid into the inner space of the hollow outer cylinder near the bottom end.

With respect to the hollow outer cylinder, the hollow outer cylinder is generally sufficiently transparent to such that informative images can be taken by a camera outside the perimeter of the hollow outer cylinder of an air bubble or a drop of immiscible fluid inside the perimeter of the hollow outer cylinder. The wall hollow outer cylinder is sufficiently thin to allow for such transparency and sufficiently thick to retain a fluid isotonic to mammalian cells under ambient pressure and the pressure generated by a depressing plunger. In varying embodiments, the hollow outer cylinder is colorless. In varying embodiments, the hollow outer cylinder is comprised of a material selected from the group consisting of glass, quartz or polymethylmethacrylate (PMMA). In varying embodiments, the hollow outer cylinder comprises an inner diameter in the range of about 10-15 mm, e.g., about 10 mm, 10.5 mm, 11 mm, 11.5 mm, 12 mm, 12.5 mm, 13 mm, 13.5 mm, 14 mm, 14.5 mm or 15 mm. The height of the hollow outer cylinder is generally less than the height of the syringe or the syringe with a flat/blunt tip needle attached. In varying embodiments, the hollow outer cylinder comprises height in the range of about 10 mm to about 50 mm, e.g., about 10 mm to about 30 mm, e.g., about 10 mm, 15 mm, 20 mm, 25 mm, 30 mm, 35 mm, 40 mm, 45 mm or 50 mm.

The hollow outer cylinder comprises a top end comprising an aperture of a diameter sufficient to allow passage of a syringe. In varying embodiments, the aperture is centered in the top end of the hollow outer cylinder. Syringes of use include commercially available, off-the-shelf 0.2 mL, 0.3 mL, 0.5 mL and 1.0 mL syringes. In varying embodiments, the syringe comprises an outer diameter in the range of about 3-10 mm, e.g., about 3 mm, 4 mm, 5 mm, 6 mm, 7 mm, 8 mm, 9 mm or 10 mm. In varying embodiments, the syringe comprises a blunt end or blunt-tipped needle. In varying embodiments, the needle comprises a gauge in the range of 22-28 (outer diameter (OD) 0.72-0.36 mm and ID 0.41-0.18 mm), e.g., 22 gauge (OD 0.72 mm), 22s gauge (OD 0.72 mm), 23 gauge (OD 0.64 mm), 24 gauge (OD 0.57 mm), 25 gauge (OD 0.51 mm), 26 gauge (OD 0.46 mm), 26s gauge (OD 0.47 mm), 27 gauge (OD 0.41 mm), or 28 gauge (OD 0.36 mm). Commercially available, off-the-shelf flat/blunt tip needles can be used in the present device.

The hollow outer cylinder further comprises a bottom end configured to form a liquid impermeable seal between an inner space of the cylinder and the surface of the eye of a mammal, which can be a human or a non-human mammal. In varying embodiments, the mammal can be a human, a non-human primate, a canine or a feline. In varying embodiments, the mammal is a rabbit. In varying embodiments, the bottom end of the hollow outer cylinder is configured to form a liquid impermeable seal between an inner space of the cylinder and the surface of the cornea of the mammal. In varying embodiments, the hollow outer cylinder itself is molded or shaped to form the liquid impermeable seal between the inner space of the cylinder and the surface of the eye of the mammal. In varying embodiments, a cuff or ring or skirt of a flexible and/or form-fitting material (e.g., composed of polydimethylsiloxane (PDMS), fluorosilicon rubber or fluoroelastomers) is attached or molded to the bottom end of the hollow outer cylinder to form the liquid impermeable seal between the inner space of the cylinder and the surface of the eye of the mammal.

In varying embodiments, the hollow outer cylinder contains a first fluid that is isotonic to the cells of the eye (e.g., corneal epithelium). The hollow outer cylinder can be fully or partially filled, as appropriate. The volume in the cylinder is generally such that the fluid level within the hollow outer cylinder will allow for complete immersion of a drop of immiscible fluid or an air bubble. In varying embodiments, the fluid that is isotonic to the cells of the eye (e.g., corneal epithelium) is transparent. In varying embodiments, the fluid that is isotonic to the cells of the eye (e.g., corneal epithelium) is colorless. In varying embodiments, the fluid that is isotonic to the cells of the eye (e.g., corneal epithelium) is selected from saline solution or artificial tears.

In varying embodiments, the syringe contains a second fluid, wherein the second fluid is immiscible with the first fluid and comprises a higher density than the first fluid. In varying embodiments, the syringe contains a second fluid selected from the group consisting of a perfluorocarbon and a silicon oil. In varying embodiments, the perfluorocarbon is selected from the group consisting of perfluorodecalin, perfluorooctane and tetradecafluorohexane.

An illustrative embodiment of the device is as depicted in FIG. 8.

3. System

Further provided are systems comprising the device for determining contact angle hysteresis on the surface of live cells. In varying embodiments, the system additionally comprises a camera. Generally, the camera is focused on the contact point of the drop of immiscible fluid or bubble with the layer of live cells (e.g., the corneal epithelium). In varying embodiments, the device and the camera are in communication with one another, e.g., via a direct electrical or wireless connection. In varying embodiments, advancing and receding contact angles can be computed with an independent video (during the sampling or after it). However, communication between the camera and the device can be beneficial for the definition of endpoints.

In varying embodiments, the plunger of the syringe is in communication with a regulator (e.g., a microsyringe pump) that depresses or retracts/pulls up the plunger at predetermined distance increments over predetermined periods of time. In varying embodiments, the regulator can be remotely controlled or function in an automated manner. To allow for the dispensing of the drops or bubbles in a controlled volume, in varying embodiments, the device, in particular, the plunger of the syringe, is in mechanical and/or direct electrical or wireless communication with a microsyringe pump.

4. Methods of Determining Contact Angle Hysteresis of a Mucosal Surface on a Subject a. On a Subject or Patient (In Vivo)

Provided is a method of determining the ability of a mucosal surface (e.g., a corneal surface), of a subject to retain moisture (i.e., the wettability of the surface). In some embodiments, the methods comprise:

a) contacting the mucosal surface (e.g., corneal surface) of the subject with a device as described above and herein, such that the device contains a first fluid isotonic to the cells of the mucosal epithelium (e.g., corneal epithelium) and a second fluid that is immiscible with the first fluid and that has a higher density than the first fluid;

b) dispensing one or more drops of the second fluid into the first fluid such that the drops of the second fluid contact the mucosal surface (e.g., corneal surface) of the subject;

c) measuring at several points of contact (i) the advancing contact angle, and (ii) the receding contact angle of the drops of the second fluid in contact with the mucosal surface (e.g., corneal surface);

d) calculating the contact angle hysteresis of the combined measurements of the several points of contact, wherein a contact angle hysteresis value at or above a threshold value indicates a normal or sufficient ability of the mucosal surface (e.g., corneal surface) to retain moisture, and a contact angle hysteresis value below the threshold value indicates an abnormal or deficient ability of the mucosal surface (e.g., corneal surface) to retain moisture (e.g., indicative of a dry eye disorder).

In performing a method of determining contact angle hysteresis of a mucosal surface, such as a corneal epithelium, the hollow outer cylinder of a device described above and herein is mounted on the mucosal surface, (e.g., the surface of the eye or the surface of the cornea) and filled with the first fluid (e.g., saline solution or artificial tears). In the middle of the hollow outer cylinder runs a syringe that serves as a dispenser for a second fluid that is immiscible with the first fluid (e.g., a perfluorocarbon, silicon oil), and has a higher density than the first fluid, so that the second fluid contacts the mucosal surface (e.g., surface of the cornea) while immersed within the first fluid. The syringe is placed above of the mucosal surface (e.g., surface of the cornea), at a height sufficient such that the drop of the second fluid can be in concurrent contact with both the blunt-tipped needle of the syringe and the mucosal surface (e.g., surface of the cornea). The second fluid, immiscible with and having higher density than the first fluid, is dispensed from the syringe in a controlled way, until a stable advancing angle is achieved and recorded. The height of the tip of the syringe with respect to the corneal surface is positioned to allow the drop to be "relaxed", e.g., such that the tip of the syringe or blunt-end needle does not push the drop against the surface, which can happen when the volume of the drop is increased and the distance of the tip of the syringe or blunt-end needle is close to the corneal surface.

While increasing the volume of the drop, the contact point between the drop and the corneal surface gets "pinned", and the angle increases until the contact point gets released. When the contact line gets released, and advances, and the contact angle remains constant even as the volume of the drop increases; this is the advancing contact angle. From that point, the contact point keeps advancing at the same angle and the values of advancing contact angle can be recorded. Subsequently, the second, immiscible fluid is pulled back into the syringe by pulling back the plunger, until a stable receding angle is reached and recorded. Inversely, when the volume of the drop is decreased (retracted or pulled back into the syringe), the contact point gets released at the "receding contact angle". When the receding contact line is released, and the contact angle is constant even as the volume of the drop retracts/decreases; this is the receding contact angle. From that point, the values of the receding contact angle can be recorded. The final calculation uses the average advancing contact angle and the average receding contact angle. Accordingly, in varying embodiments, the contact angle hysteresis value of the average advancing contact angle and the average receding contact angle of the combined measurements of the several points of contact is calculated by applying the equation: the cosine of the average receding contact angle minus the cosine of the average advancing contact angle (cos $\theta_{rec}$-cos $\theta_{adv}$).

In the operation to determine contact angle hysteresis, a camera is placed on the side of the device positioned and focused to image the drop and record the contact angle. A camera is pointed to the drop and pictures are taken at predetermined time increments (e.g., every 2.0 sec, 1.5 sec, 1.0 sec, 0.5 sec) while the volume of the drop is increased/decreased. The images of the drops can be analyzed with image analysis software, where 50-100 pixels of the drop profile closer to the contact point are fitted to a curve and 50-100 pixels of the corneal surface closer to the contact point are also fitted. The contact angle can be calculated with those fitted curves. Commercially and publicly available image analysis software of use includes without limitation, e.g., ImageJ (US National Institutes of Health; on the internet at imagej.net), Interactive Data Language (IDL) (on the internet at exelisvis.com), and Image-Pro Plus (on the internet at mediacy.com).

Useful information can be obtained in determining both the static contact angle of a known liquid or gas interacting with the mucosal surface (e.g., ocular surface) as well as from determination of the hysteresis (cosine of average receding contact angle minus cosine of average advancing contact angle). They provide distinct and distinctly useful information.

In varying embodiments, the method further comprises moving the device to a second or subsequent point of contact on the corneal surface and repeating steps of dispensing drops, measuring contact angles and calculating the contact angle hysteresis. In varying embodiments, the one or more drops comprise an average diameter of about 1-5 mm, e.g., about 1 mm, 1.5 mm, 2.0 mm, 2.5 mm, 3.0 mm, 3.5 mm, 4.0 mm, 4.5 mm, 5.0 mm. In varying embodiments, the methods further comprise measuring the static contact angle. In varying embodiments, the measuring step is performed by obtaining a collection of digital images of the drops of the second fluid in contact with the corneal surface. In varying embodiments, the advancing contact angle values are measured at predetermined time increments (e.g., every 2.0 sec, 1.5 sec, 1.0 sec, 0.5 sec) while the contact point of the drop advances across the corneal surface. In varying embodiments, the receding contact angle values are measured at predetermined time increments (e.g., every 2.0 sec, 1.5 sec, 1.0 sec, 0.5 sec) while the contact point of the drop recedes across the corneal surface. In varying embodiments, the contact angle hysteresis value of the average advancing contact angle and the average receding contact angle from the combined measurements of the several points of contact is calculated by applying the equation: cosine of the average receding contact angle minus the cosine of the average advancing contact angle (cos $\theta$rec−cos $\theta$adv). In varying embodiments, the threshold value is in the range of about 0.6 to about 1.0, e.g., about 0.7 to 0.9, e.g., about 0.60. 0.61, 0.62, 0.63, 0.64, 0.65, 0.66, 0.67, 0.68, 0.69, 0.70. 0.71, 0.72, 0.73, 0.74, 0.75, 0.76, 0.77, 0.78, 0.79, 0.80. 0.81, 0.82, 0.83, 0.84, 0.85, 0.86, 0.87, 0.88, 0.89, 0.90, 0.91, 0.92, 0.93, 0.94, 0.95, 0.96, 0.97, 0.98, 0.99 or 1.0.

5. Subjects Who can Benefit from Determination of Contact Angle Hysteresis

Patients who can benefit from evaluation of contact angle hysteresis, e.g., of their corneal epithelium, include individuals at risk of disease but not showing symptoms, as well as patients presently showing symptoms of a dry eye disease. The dry eye disease may be an aqueous-deficient dry eye disease (due to insufficient tear production) or an evaporative dry eye disease (e.g., excessive tear film evaporation, e.g., due to a loss of amount and/or integrity of the lipid component of the precorneal tear film), or have components of both an aqueous-deficient dry eye disease and an evaporative dry eye disease.

In various embodiments, the subject may already exhibit symptoms of disease or be diagnosed as having a dry eye disease. For example, the subject may be exhibiting one or more symptoms, including eye irritation (e.g., dryness, burning, sandy-gritty sensations, itching, stinging, fatigue, pain, redness, pulling sensations), stingy discharge from the eyes, and the production of non-lubricating tears; squamous metaplasia and loss of goblet cells in the epithelium; and/or damage to the cornea (e.g., thickening of the corneal surface, corneal erosion, punctate keratopathy, epithelial defects, corneal ulceration (sterile and infected), corneal neovascularization, corneal scarring, corneal thinning, and/or corneal perforation).

In some embodiments, the subject has an autoimmune disease. For example, the subject may have an autoimmune disease the result in immune-mediated destruction of the lacrimal gland and/or the meibomian glands and/or goblet cells of the conjunctiva. Subjects who have or are diagnosed with an autoimmune disease that causes or is associated with symptoms of dry eye disease, including without limitation, rheumatoid arthritis, Wegener's granulomatosis, systemic lupus erythematosus (SLE), Sjögren's syndrome, scleroderma, primary biliary cirrhosis, diabetes or Vogt-Koyanagi-Harada Syndrome (VKH Syndrome) are candidates for treatment or prevention of dry eye disease by administration of MSCs. In some embodiments, the subject has an autoimmune disease or has a predisposition to developing Stevens-Johnson syndrome. The subject may or may not exhibit symptoms of dry eye disease.

6. In Vitro Methods of Determining Contact Angle Hysteresis

Methods for determining contact angle hysteresis in vitro can be practiced following at least two different approaches: (1) positioning a support substrate coated with a layer of cells at or near the bottom of a reservoir containing a first fluid isotonic to mammalian cells, and contacting the layer of cells with one or more drops of a second fluid that is immiscible with and having a higher density to the first fluid; and (2) positioning a support substrate coated with a layer of cells at or near the top of a reservoir containing a first fluid isotonic to mammalian cells, and contacting the layer of cells with one or more air bubbles or a gas that is immiscible with the first fluid.

With respect to the first approach, in varying embodiments, the method comprises:

a) immersing a layer of live or viable cells attached to a support substrate in a reservoir comprising a solution that is isotonic to mammalian cells, wherein the support substrate is positioned at or near the bottom of the reservoir and the layer of cells is above the support substrate;

b) introducing into the solution one or more drops of a second solution that is immiscible with the isotonic solution, wherein the drops contact the layer of cells;

c) measuring at several points of contact (i) the advancing contact angle, and (ii) the receding contact angle of the drops of the second solution in contact with the layer of cells;

d) calculating the contact angle hysteresis of the combined measurements of the several points of contact. In some embodiments, the second solution is selected from the group consisting of a perfluorocarbon and a silicon oil. In some embodiments, the perfluorocarbon is selected from the group consisting of perfluorodecalin, perfluorooctane and tetradecafluorohexane.

In practicing the first approach, one or more drops are placed on the layer of live or viable cells attached to a support substrate submerged in a solution that is isotonic to mammalian cells in a reservoir, and the support substrate (optionally and the reservoir) is tilted. If there is no hysteresis, the drop just rolls off the surface. If there is hysteresis, the drop gets "pinned" or "trapped" on the topographical features of the layer of cells on the support substrate, until a critical tilting, where the drop starts rolling off. At the point of moving, the advancing (the lowest) and the receding (the highest) angles are recorded. The support substrate can be tilted at a predetermined rate, e.g., at a rate of 1 degree per second. The drop moves faster on the unstratified cells, because it detaches before, at a lower tilting angle (the tilting angle is different from the advancing and receding angle).

The values of interest for recording are the advancing and receding angles at the point when the drop detaches.

With respect to the first approach, in varying embodiments, the method comprises:

a) immersing a layer of live or viable cells attached to a support substrate in a transparent reservoir comprising an solution that is isotonic to mammalian cells, wherein the support substrate is inverted and positioned at or near the top of the reservoir, and the layer of cells is below the support substrate;

b) introducing into the solution one or more air or gas bubbles, wherein the bubbles contact the layer of cells;

c) measuring at several points of contact (i) the advancing contact angle, and (ii) the receding contact angle of the bubbles in contact with the layer of cells;

d) calculating the contact angle hysteresis of the combined measurements of the several points of contact.

In practicing the second approach, one or more bubbles are delivered into the solution that is isotonic to mammalian cells such that is rises to contact the layer of live or viable cells attached to the inverted support substrate submerged in the solution in a reservoir, and the support substrate (optionally and the reservoir) is tilted. If there is no hysteresis, the bubble just rolls off the surface. If there is hysteresis, the bubble gets "pinned" or "trapped" on the topographical features of the layer of cells on the support substrate, until a critical tilting, where the bubble starts rolling off. At the point of moving, the advancing (the lowest) and the receding (the highest) angles are recorded. The support substrate can be tilted at a predetermined rate, e.g., at a rate of 1 degree per second. The bubble moves faster on the unstratified cells, because it detaches before, at a lower tilting angle (the tilting angle is different from the advancing and receding angle). The values of interest for recording are the advancing and receding angles at the point when the bubble detaches.

With respect to embodiments of the methods for determining the contact angle hysteresis on a surface or layer of live/viable cells, in varying embodiments, the method maintains hydration of the cell surface and/or avoids disruption of the chemical components of the cellular membrane. In varying embodiments, the cells are mammalian corneal cells. In varying embodiments, the mammalian corneal cells are selected from human, canine and feline corneal cells. In varying embodiments, the solution that is isotonic to a mammalian cell is transparent. In varying embodiments, the solution that is isotonic to a mammalian cell is colorless. In varying embodiments, the solution that is isotonic a mammalian cell is a saline solution, e.g., phosphate buffered saline (PBS). In varying embodiments, the support substrate is comprised of a material selected from the group consisting of glass, silicon, polystyrene, or any other tissue culture material. In varying embodiments, the several points of contact cover substantially the entirety of the layer of cells attached to the support substrate. In varying embodiments, the one or more drops or bubbles comprise an average diameter of about 1-5 mm, e.g., about 1 mm, 1.5 mm, 2.0 mm, 2.5 mm, 3.0 mm, 3.5 mm, 4.0 mm, 4.5 mm, 5.0 mm. In varying embodiments, the methods further comprise measuring the static contact angle. In varying embodiments, the measuring step is performed by obtaining a collection of digital images of the drops or bubbles in contact with the layer of cells. In varying embodiments, the advancing contact angle values are measured at predetermined time increments (e.g., every 2.0 sec, 1.5 sec, 1.0 sec, 0.5 sec) while the contact point of the drops or bubbles advances across the layer of cells. In varying embodiments, the receding contact angle values are measured at predetermined time increments (e.g., every 2.0 sec, 1.5 sec, 1.0 sec, 0.5 sec) while the contact point of the drops or bubbles recedes across the layer of cells. In varying embodiments, the support substrate is tilted to adjust the rate that the drops or bubbles move across the layer of cells. In varying embodiments, the contact angle hysteresis value of the average advancing contact angle and the average receding contact angle from the combined measurements of the several points of contact is calculated by applying the equation: cosine of the average receding contact angle minus the cosine of the average advancing contact angle ($\cos \theta_{rec} - \cos \theta_{adv}$).

7. Kits

Further provided are kits that comprise a device for determining contact angle hysteresis, as described herein. In varying embodiments, the kits can comprise several hollow outer cylinders, e.g., with different varying geometries (e.g., varying diameters, varying heights, and varying geometries of the flexible skirt attached or molded to the bottom end of the hollow outer cylinder). In varying embodiments, the kits comprise a system, e.g., a device for determining contact angle hysteresis, as described herein, a camera for use with the device and a regulator (e.g., a microsyringe pump). The kits may further comprise a supporting substrate for cultured cells.

EXAMPLES

The following examples are offered to illustrate, but not to limit the claimed invention.

Example 1

Effect of Stratification on the Surface Properties of Corneal Epithelial Cells Methods Cell Culture.

Human telomerase reverse transcriptase-immortalized corneal epithelial (hTCEpi) cells were graciously donated by Dr. James Jester from the University of California, Irvine (11). Cells were used between passages 50 to 60. hTCEpi cells were cultured in Growth Medium (GM), composed of Epilife® (Life Technologies, CA) supplemented with Epilife® Defined Growth Supplement (EDGS, a proprietary combination of bovine serum albumin, bovine transferrin, hydrocortisone, recombinant human-like growth factor type-1, prostaglandin and recombinant human epidermal growth factor, Life Technologies, CA). Cells were incubated on the surface of glass slides treated with a proprietary mixture of fibronectin-collagen coating (FNC, Athena Enzyme Systems, Baltimore, Md.) as described previously (14,15) at 37° C. and 5% $CO_2$ until they reached 100% confluence, and the GM was replaced by stratification media (SM) containing DME/F12 medium (Invitrogen), 10% FBS, 10 ng/mL EGF, 100 units penicillin, and 100 μg/ml streptomycin to induce differentiation and stratification (10).

Quantitative Polymerase Chain Reaction (Q-PCR).

Total RNA was extracted from three replicates for hTCEpi cells cultured to 100% confluence in GM, and for hTCEPi cells cultured in SM at day 1 through 7 following the Qiagen RNeasy Kit protocol (Qiagen, Germantown, Md.). Briefly, cells were lysed in 350 μl Qiagen RLT buffer containing 10 μl/ml of 2-mercaptoethanol (Sigma-Aldrich, St Louis, Mo.). An equal amount of 70% ethanol was added to each sample, and mixed prior to loading onto Qiagen H-Bind columns. Columns were washed with Qiagen buffers RW1 and RPE and eluted with 30 µL of nuclease-free water. Sample concentrations were measured at OD 260 for total RNA using a NanoDrop 2000 spectrophotometer (Thermo Scientific, Wilmington, Del.). The concentration of RNA was calculated using the equation: $C=(A*\varepsilon)/b$ where C is the nucleic acid concentration (ng/µL), A is the absorbance at 260 nm, $\varepsilon$ is the extinction coefficient (40 ng·cm/µL for RNA) and b is the path length in cm. Samples were further diluted with nuclease-free water to a concentration of 75 ng/mL and stored at −20° C.

Primers were purchased from the pre-developed and commercially available TaqMan assay reagents (Life Technologies, Carlsbad, Calif.). The assay ID numbers for the TaqMan probes are as follows: MUC1: Hs00159357-m116, MUC4: Hs00366414-m1, and MUC16: Hs01065189-m1. Gene expression levels were normalized to 18S RNA (reference number Hs99999901-s1). As we used commercially available TaqMan probes, the amplicons were not validated using secondary methods. Q-PCR was performed using SensiFAST Probe Hi-ROX one-step kit (Bioline, Taunton, Mass.) using 75 ng of total RNA per sample on a StepOne RT-PCR system (Applied Biosystems, Carlsbad, Calif.). Reaction conditions were as follows: 50° C. for 20 min, 95° C. for 10 min, and 40 cycles of 95° C. for 15 s and 60° C. for 1 min. The relative quantification of gene expression was performed using the $\Delta\Delta CT$ method (17) using the StepOne Real-Time PCR software (Applied Biosystems, Carlsbad, Calif.). Blank controls were run to ensure the specificity of the amplifications.

Western Blots.

Cell cultures were washed once in PBS and lysed and scraped into 2% sodium dodecyl sulphate (SDS, Fisher, Japan) in PBS, supplemented with Halt® protease and phosphatase inhibitor cocktail (Thermo Scientific, Rockford, Ill.). The cells were homogenized and centrifuged at 1000 g for 1 minute to remove cell debris. Protein was quantified using a modified Lowry assay (DC assay, Bio-Rad Laboratories, Hercules, Calif.) using bovine serum albumin as the standard. Protein homogenate was denatured in NuPAGE LDS sample buffer (Life Technologies, Carlsbad, Calif.) and 50 µg of protein was loaded on 0.7% agarose gels (SeaKem LE Agarose, Lonza, Rockland, Me.) and transferred onto a polyvinylidene fluoride (PVDF, Immobilon-P, Millipore, Billerica, Mass.). The membrane was blocked for 2 hours at 25° C. in milk diluent/blocking (KPL, Gaithersburg, Md.). The antibodies used for immunoblotting were anti-human MUC1/episialin clone 214D4 (Millipore, Temecula, Calif.), MUC4 clone 8G7 (Abcam, Cambridge, Mass.) and MUC16 clone OC125 (Abcam, Cambridge, Mass.) for 1 h at 37° C. This was followed by incubation with horseradish peroxidase labeled goat anti-mouse antibody (KPL, Gaithersburg, Md.) for 1 h at 25° C. and the bands were detected by chemiluminescence (Westernbright Quantum Western Blotting detection for HRP conjugates; Advansta, Menlo Park, Calif.) and imaged using a Chemi-Doc-It imaging system (UVP, Upland, CA).

Contact Angle/Surface Energy and Hysteresis.

Contact angles were determined using a Ramé-Hart model 290 contact angle goniometer equipped with an environmental fixture and automated tilting base. The surfaces were placed in the environmental fixture filled with Dulbecco's Phosphate Buffered Saline (DPBS). For captive bubble measurements, the cellular surfaces were placed facing down and for sessile drop measurements with perfluorocarbons (perfluorodecalin, perfluorooctane and tetradecafluorohexane, Sigma-Aldrich, St Louis, Mo.) the cellular surfaces were placed facing up. The choice of the perfluorocarbons was based on their insolubility in aqueous solutions, their non-toxicity, their inertness and their precedent usage for biomedical applications (18-20). The air bubbles or perfluorocarbon drops (10 µL) were placed in contact with the cellular surface. The stage was tilted at a rate of 0.5 degrees/second and the advancing and receding angle values were measured every second until the bubble/drop rolled off the surface. The hysteresis of the contact angle was determined by recording the advancing and receding angle at the moment just before the drop rolled-off and calculating the difference of the cosine of both angles ($\cos\theta_{adv} - \cos\theta_{rec}$) (21). According to Furmidge, the value of ($\cos\theta_{adv} - \cos\theta_{rec}$) when the drop starts to slide is a constant, independent of the size of the drop and the angle of tilt (22).

Atomic Force Microscopy (AFM).

Cells were fixed in 5% glutaraldehyde and 4% paraformaldehyde in DPBS for 30 minutes, washed in DPBS and imaged by atomic force microscopy using the MFP-3D BIO AFM (Asylum Research, Santa Barbara, Calif.) coupled with a Zeiss Axio Observer inverted microscopy (Carl Zeiss, Thornwood, N.Y.). Imaging was performed in fluid, contact mode using silicon nitride cantilevers (PNP-TR-50, nominal spring constant (k) of 0.22 N/m and half angle opening of 35 degrees, NanoAndMore, Lady's Island, S.C.) at 500 pN applied force and 0.3 Hz. Root mean square (RMS) values were extracted from the images using inbuilt functions of the Asylum Research AFM software (v12, Oxford Instruments, CA).

Labeling of O-glycans on the Cell Surface.

To label the O-glycans on the surface of the cell cultures, the cell cultures were incubated with 10 µg/cm$^2$ of biotinylated Jacalin (Vector Labs, Burlingame, Calif.), a plant based lectin, for 30 minutes, followed by rinsing with DPBS. The cells were then cultured in 0.625 µM of SYTO11 nuclear dye (Molecular Probes, Eugene, Oreg.) supplemented with 5 µL/mL of streptavidin-conjugated quantum dots (Qdot® 585, Molecular Probes, Eugene, Oreg.) for 30 minutes. The cultures were then rinsed twice with DPBS and the epifluorescence was imaged using an epifluorescent microscope (Zeiss Axiovert 200M, CarlZeiss AG, Germany). Controls using competitive inhibition with 1 mM β-lactose (Sigma-Aldrich, St Louis, Mo.) and non-competitive controls with 1 mM sucrose (Sigma-Aldrich, St Louis, Mo.) were used to ensure specificity of binding of Jacalin to β-galactosides. 10 µg/cm$^2$ of biotinylated bovine serum albumin (BSA, Sigma-Aldrich, St Louis, Mo.) was used as non-specific binding controls.

Statistical Analysis.

Experiments were analyzed using one-way analysis of variance (ANOVA). When variability was determined to be significant (P<0.05), the Tukey multiple comparison test was performed to determine significance between groups.

Figure 2:
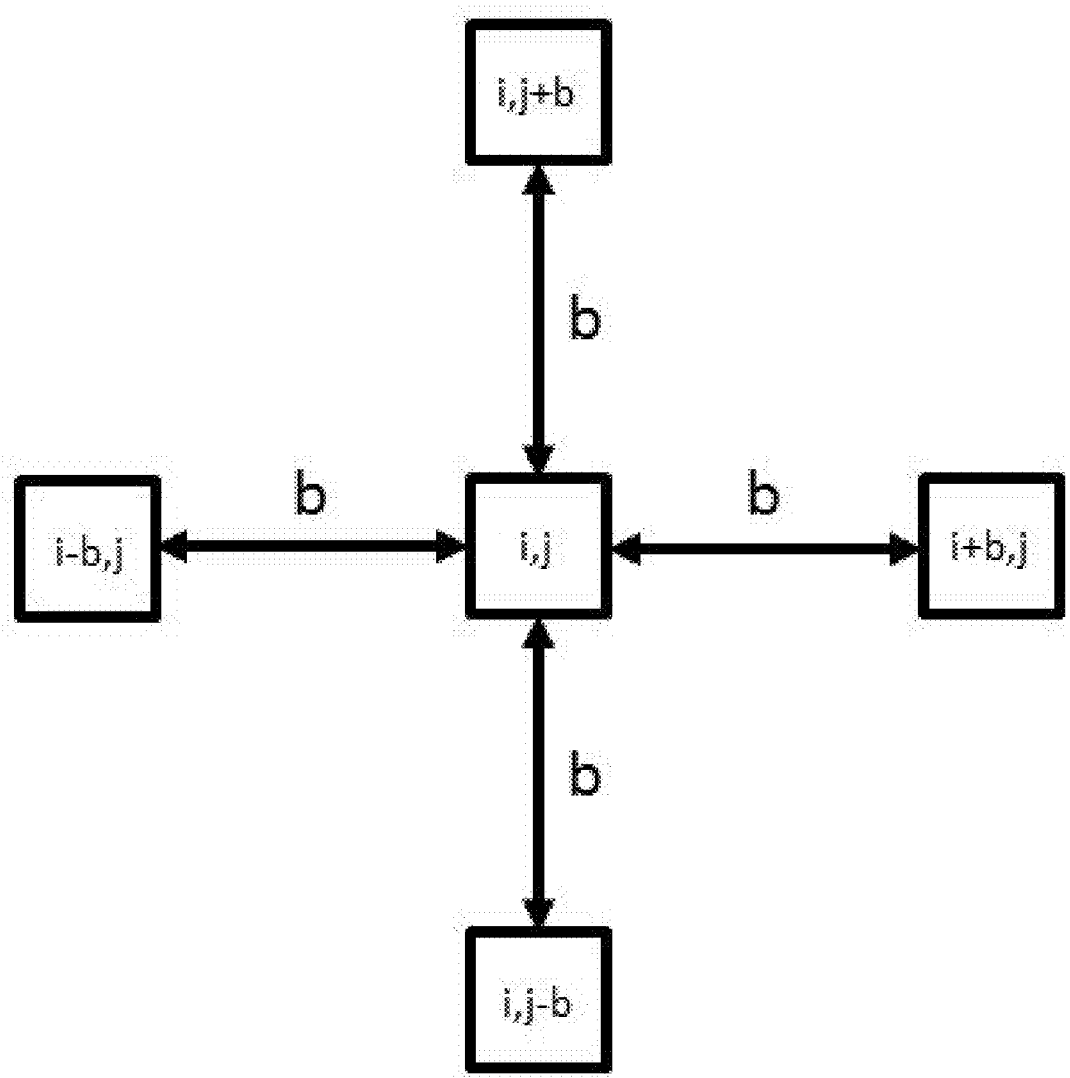
FIG. 2 illustrates pentuplet quadrant variance method (5QV). The variance between the intensity of the central pixel (i,j), and the pixels at a distance b on the four cardinal points is calculated.

The heterogeneity and scale of the pattern of the distribution of glycosylated molecules was measured using the pentuplet quadrat variance method (5QV)23. This method computes the variance between a pixel and the pixels that are at a distance 'b' from the initial one on the four cardinal points (FIG. 2). The variance for each b value is:

$$V_5(b) = \frac{\sum_{i=b+1}^{n_x-b} \sum_{j=b+1}^{n_y-b} (d_{i-b,j} + d_{i+b,j} + d_{i,j-b} + d_{i,j+b} - 4d_{i,j})^2}{20(n_x - 2b)(n_y - 2b)}$$

The variance is charted against the several b distances. The higher the variance, the more heterogeneous is the surface; and peaks on the variance are correlated to the scale of the patterning. The pixel size of the images analyzed with the 5QV method was of 0.32 µm/pixel.

Results

Mucin Expression.

Figure 3:
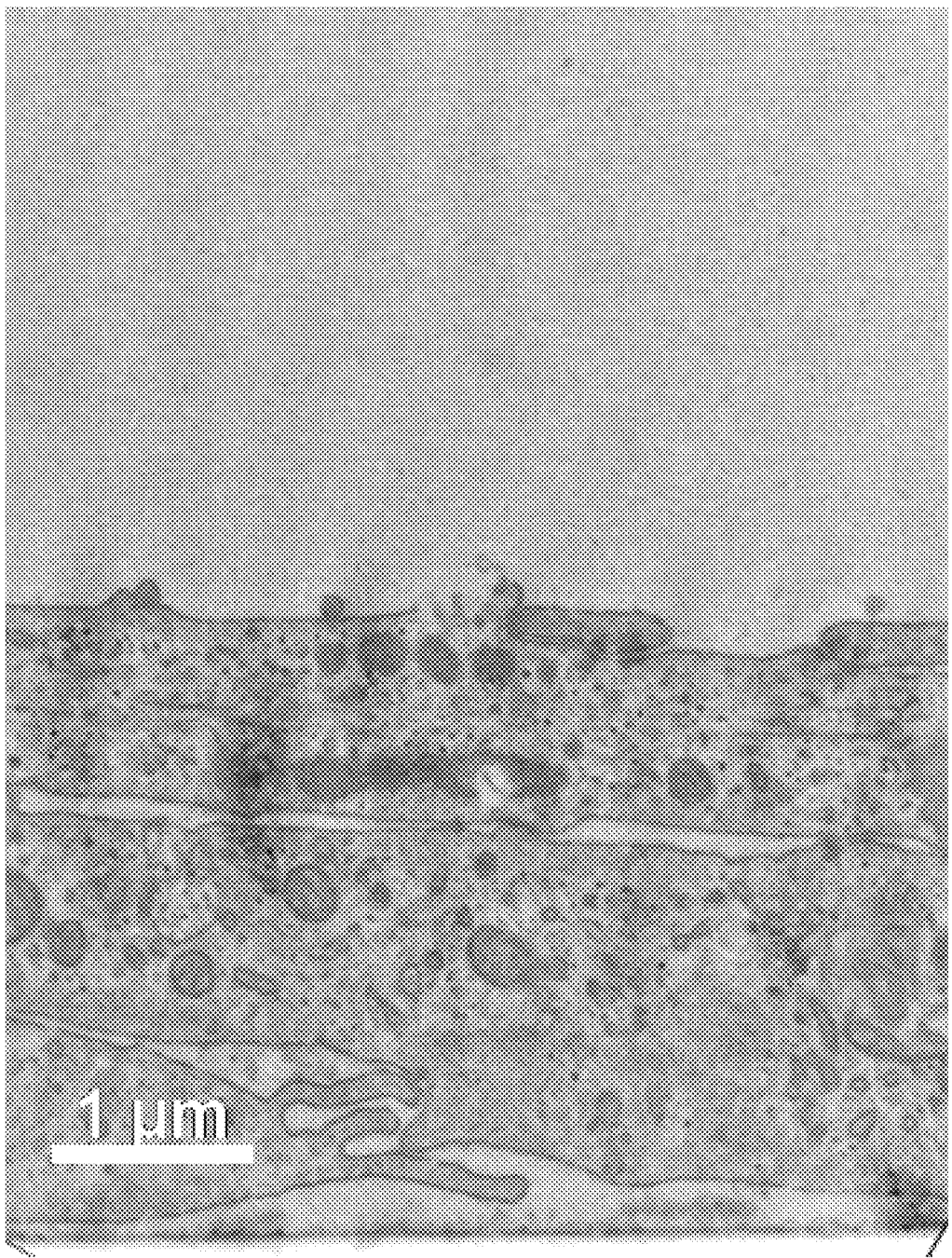
FIG. 3 illustrates a transmission electronic micrograph of cells cultured in Stratifying Medium (SM) for three days.

Stratification of hTCEpi cells was induced when cultured in SM (FIG. 3). Q-PCR was used to evaluate the mRNA expression of the most relevant mucins of the ocular surface (MUC1, MUC4 and MUC16) during the differentiation and stratification process. Undifferentiated hTCEpi cells showed little MUC1 mRNA expression and negligible MUC4 and MUC16 expression (Day 0, FIG. 4A). When the GM was replaced by SM, hTCEpi cells markedly increased expression of all three cell associated mucin genes (Days 1-6, FIG. 4A) with maximum expression seen between days 1-3.

Mucin protein expressions were validated by Western blots. Due to the large size of the mucin proteins, the smaller proteins such as those used as endogenous controls were lost during the electrophoresis, thus our evaluation of protein expression was qualitative. MUC1 and MUC16 expression profiles reflected the findings for mRNA expression, with a maximum expression between days 1-3 and then a decrease between days 4-6 (FIG. 4B). Protein expression of MUC4 was observed to continuously increase up to day 6 (FIG. 4B) in contrast with its mRNA expression profile (FIG. 4A).

Contact Angle and Contact Angle Hysteresis.

Figure 6:
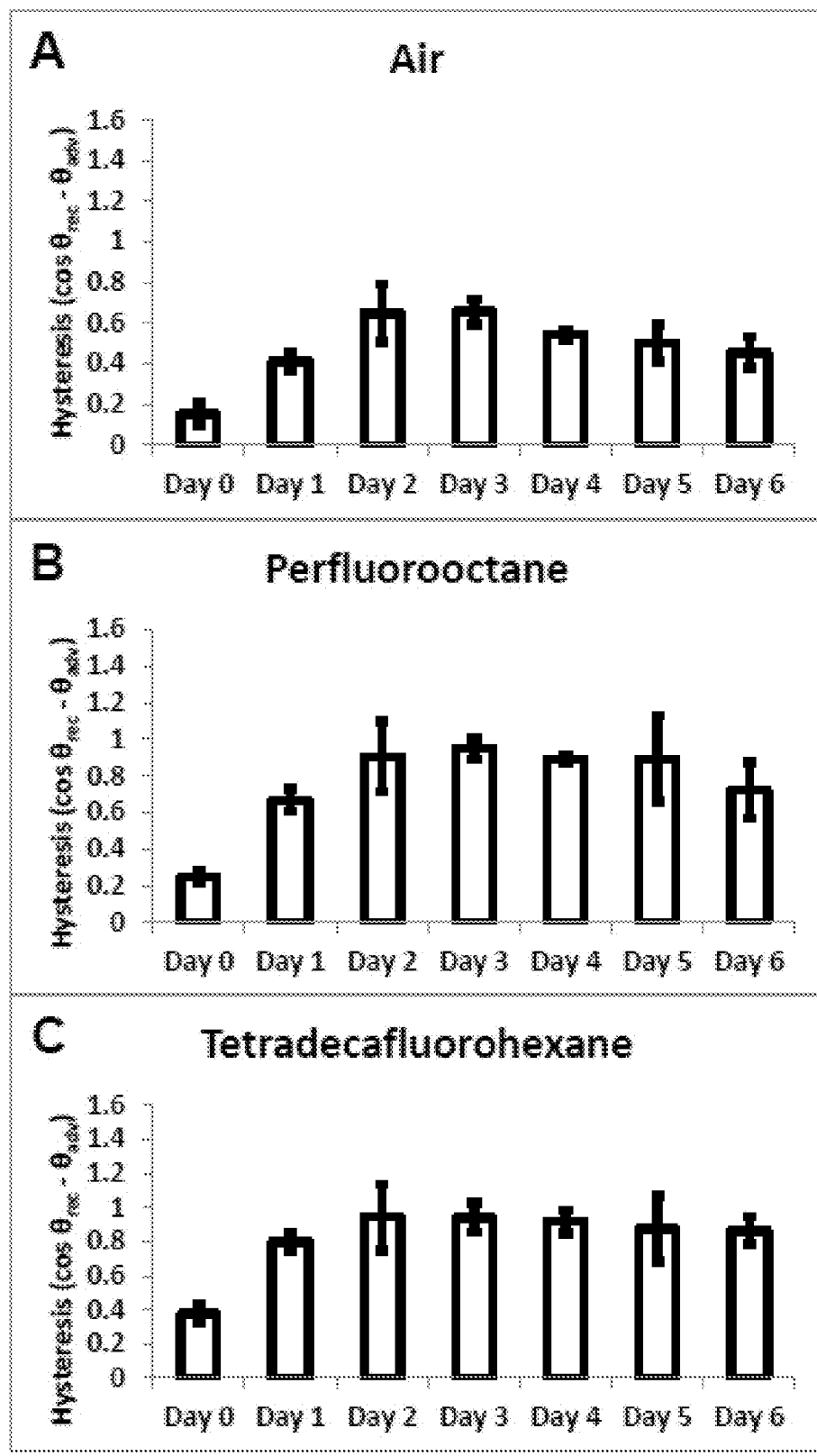
FIGS. 6A-C illustrate hysteresis ($\cos \theta_{rec} - \cos \theta_{adv}$) using A) air bubble, B) Perfluorooctane and C) Tetradecafluorohexane as the immiscible phase.

To test if the changes in surface mucin expression influenced the wettability of the corneal epithelium, we devised a two-liquid method to measure the contact angle. The cell cultures were immersed in PBS, with the cell surface of the substrates facing down for the case of captive air bubble and facing up for sessile perfluorocarbon drops. On first inspection, the measured contact angles (initial static contact angle) were similar between all samples, from day 0 to day 6 (145-150°). However, when the surfaces were tilted, we observed a very significant increase in the contact angle hysteresis for the cells cultured in SM, as compared to the unstratified cells cultured in GM (FIG. 5A). To illustrate this behavior, in FIG. 5B we show the contact angle hysteresis profile of perfluorodecalin drops, where the hysteresis observed increased to a maximum for the SM cells between days 2-3 before progressively decreasing. This profile very closely mimicked the mucin expression profile. For perfluorooctane drops, tetradecafluorohexane drops and air bubbles, the hysteresis profile was identical to the perfluorodecalin drops (FIG. 6).

Topography.

To elucidate the possible cause for the large change in hysteresis of the contact angle, we evaluated the surface topography of hTCEpi cells at different stratification levels, imaging the cells using AFM. hTCEpi cells cultured on GM showed a cobblestone morphology with tall and discrete polygonal cells. Once exposed to SM, the topmost layer of cells appeared flatter with well-marked cell junctions. Except some very small surface protrusions, no other topographic feature was apparent on those images (FIG. 7). RMS values for control epithelial cells (Day 0) in GM was approximately 1060±120 nm (mean±standard deviation), while that for cells in SM was Day 1: 470±80 nm, Day 2: 450±120 nm, Day 3: 500±80 nm, Day 4: 530±90 nm, Day 5: 580±110 nm, and Day 6: 460±30 nm (FIG. 8). These figures demonstrate a significant flattening of the cells once the media is changed to SM. No significant differences in roughness were observed between the culture day of cells cultured in SM.

Surface Glycosylation Heterogeneity.

Figure 9A:
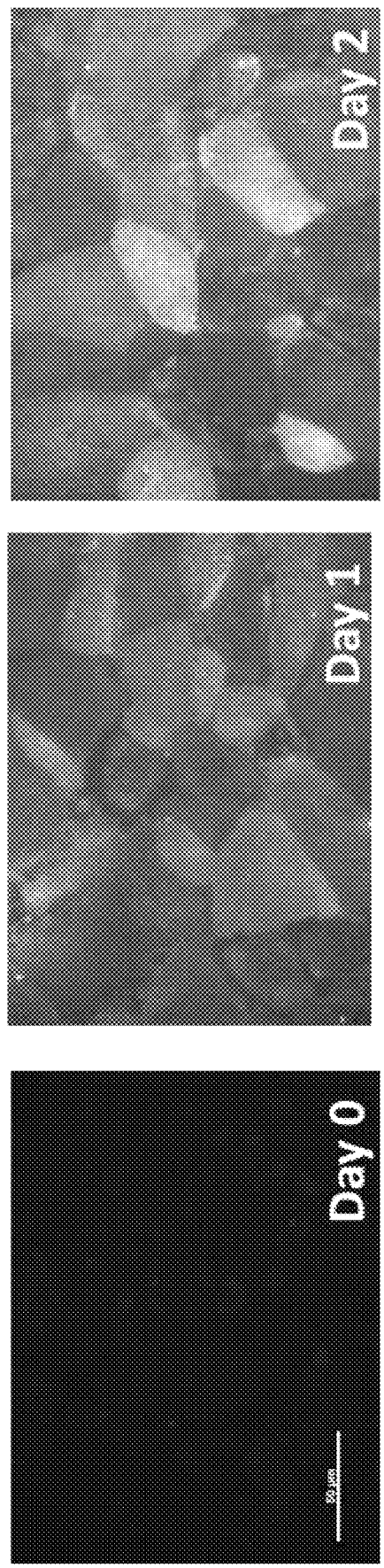
FIGS. 9A-C illustrate surface O-glycosylation imaged with fluorescent jacalin for the hTCEpi cell cultures at day 0 (unstratified cells) and days 1-6 during the stratification process. The jacalin binding for unstratified cells is low and appears to be uniformly distributed. The staining increases when the stratification process starts, showing a high heterogeneity of the surface O-glycosylation. (Scale bar: 50 µm)
Figure 9B:
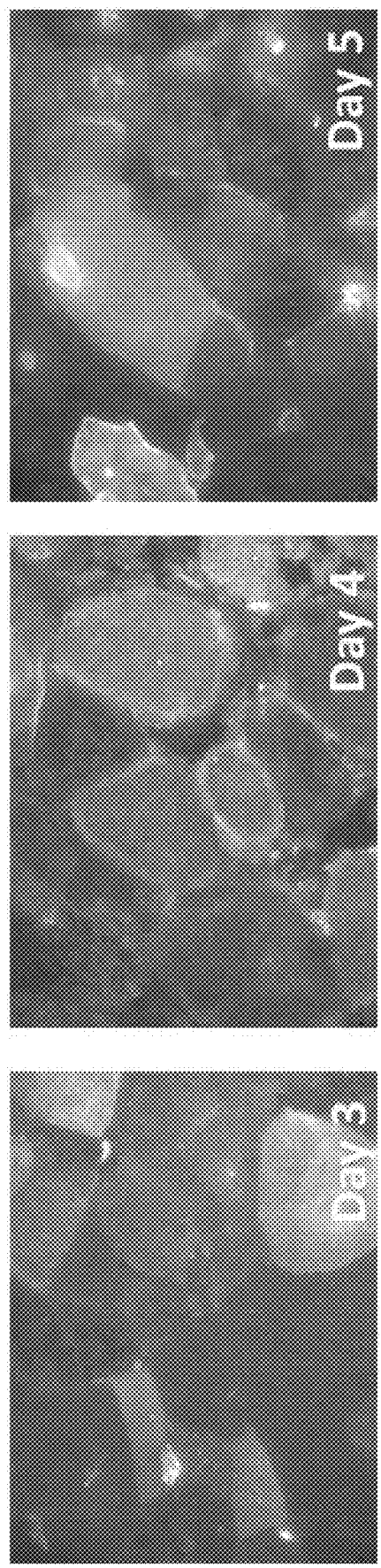
Figure 9C:
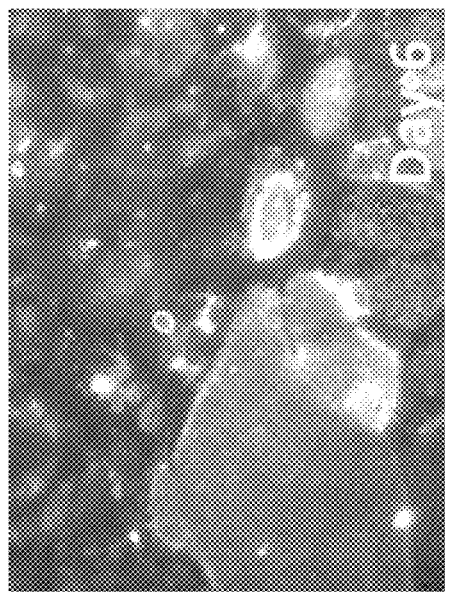

To determine the expression and spatial distribution of glycoproteins on the corneal epithelium surface, hTCEpi at different degrees of differentiation were incubated with Jacalin-Qdots (for O-glycans), or BSA-Qdots (as a non-specific binding control), and imaged for epifluorescence. Unstratified cells demonstrated very little yet uniformly-distributed Jacalin binding. However, cells cultured in SM showed a dramatic change in both the extent of Jacalin binding and the heterogeneity of the surfaces (FIG. 9). The lactose supplemented controls inhibited the binding of the Qdots to the surface glycosides, while the sucrose supplemented controls did not inhibited the binding, demonstrating specificity of Jacalin to β-galactosides. The controls using BSA showed no non-specific binding.

Figure 10:
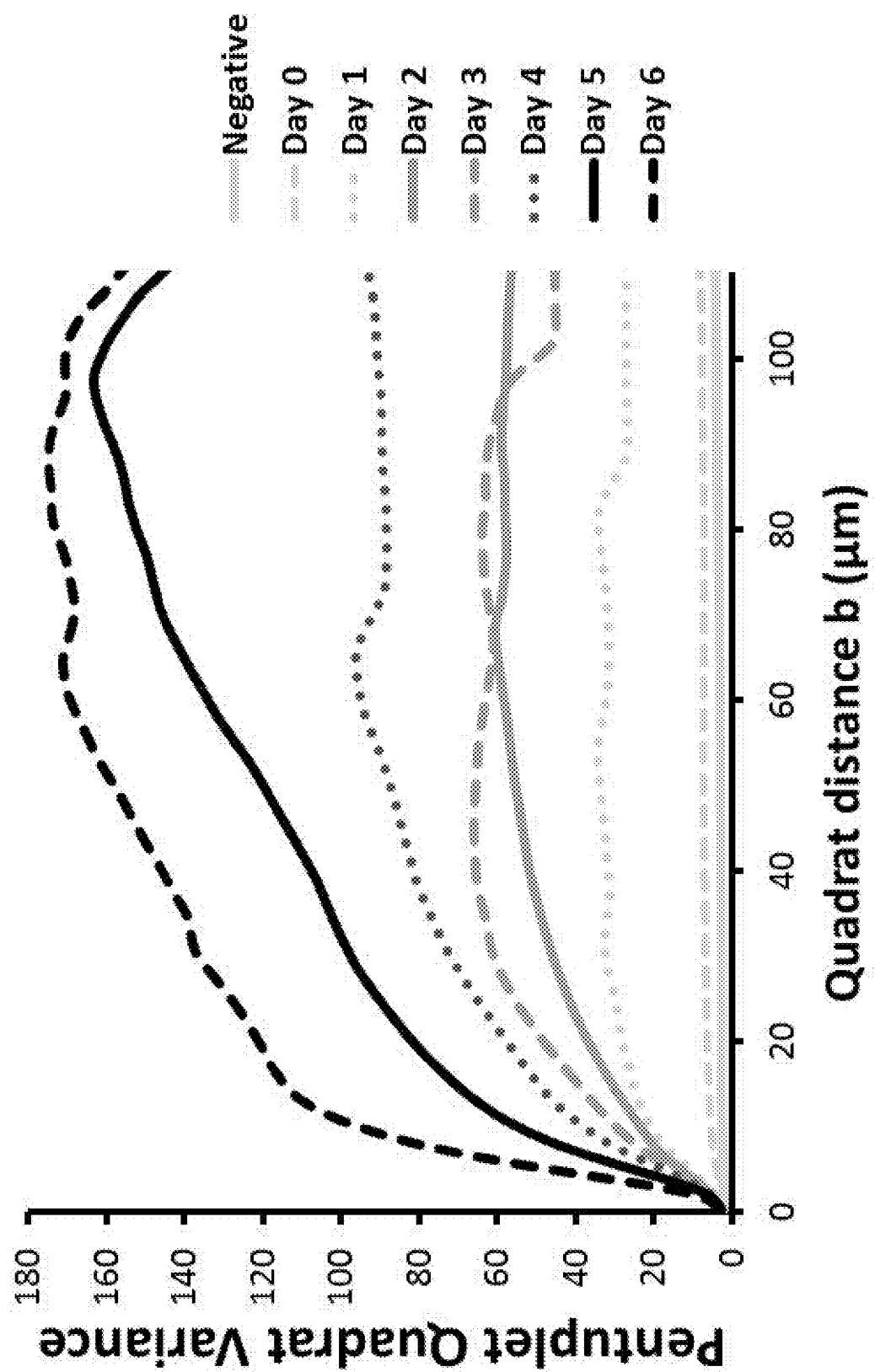
FIG. 10 illustrates pentuplet Quadrat Variance (5QV) of the fluorescent-jacalin cell cultures at day 0 (unstratified) and days 1-6 during the stratification process. The variance represents the surface O-glycosylation heterogeneity. Unstratified cells show very little heterogeneity, and this increases with the differentiation process. The maxima of the graphs correlate with the size of the heterogeneities.
Figure 11:
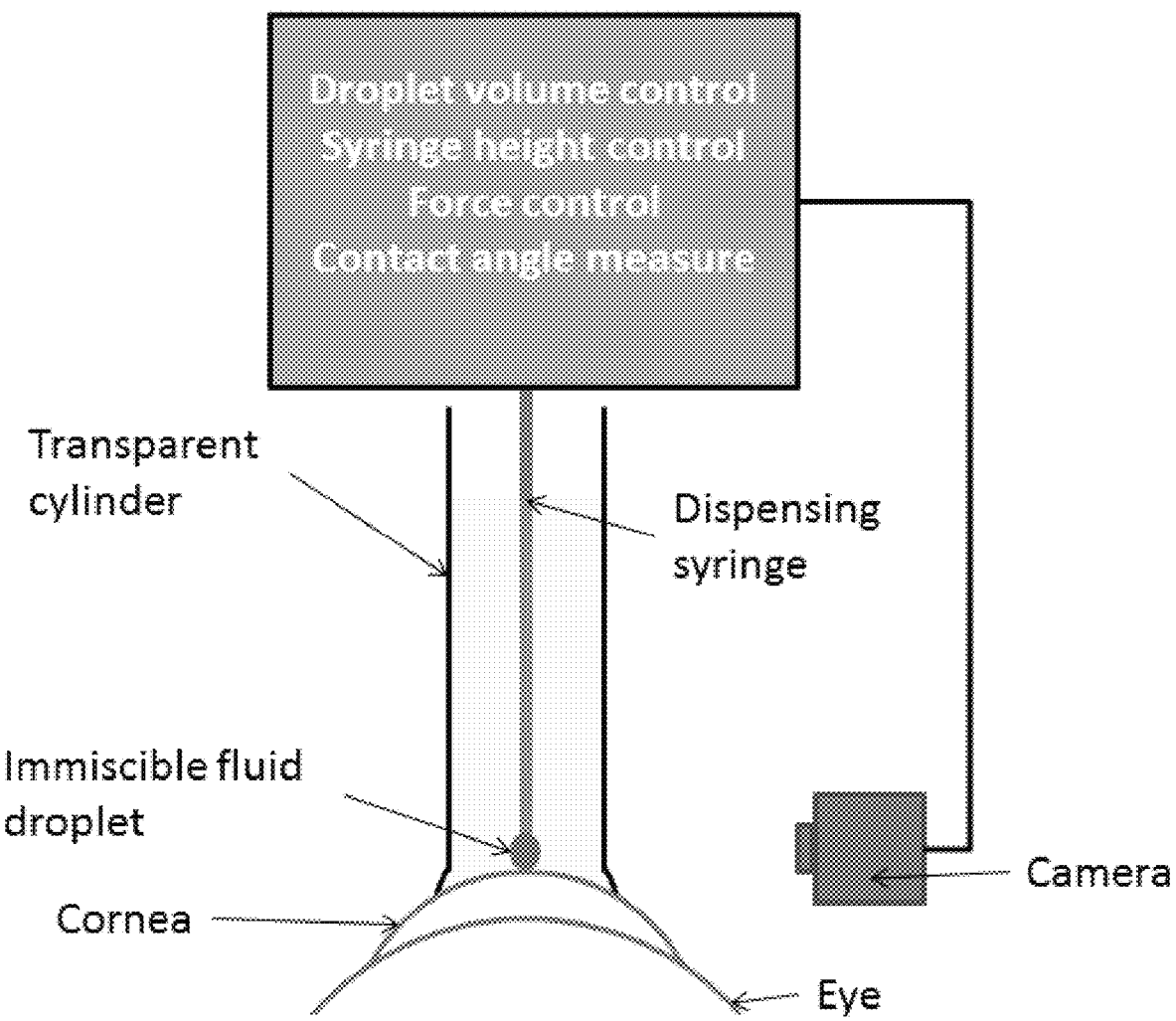
FIG. 11 illustrates a device for measuring contact angle hysteresis on the corneal epithelium of a subject. The device has a transparent cylinder with a form-fitting material at the bottom end to be placed over the patient's cornea. Inside the cylinder is a syringe that dispenses controlled volumes of an immiscible fluid to the surface of the cornea. The transparent outer cylinder is filled with saline solution, and the immiscible fluid droplet is imaged to quantify the contact angle formed between the surface of the cornea and the immiscible fluid.

The quantification of the surface heterogeneity with the quadrant variance method shows that the surface distribution of mucins of unstratified cells is homogeneous (flat curve with low variance), while the spatial heterogeneity dramatically increases with stratification. The maxima of the variance indicate the scale of the glycosylated patches (20-80 µm, which roughly corresponds to the diameter of the cells) (FIG. 10). This suggests that among the population of surface cells, certain cells dramatically upregulate mucin expression while others do not.

DISCUSSION

Although one of the attributed roles of the membrane-associated mucins of the corneal epithelium (mainly MUC1, MUC4 and MUC16) (9) has been to facilitate the wettability of the corneal epithelium (24-26), most of the studies involving the measurement of the hydrophilicity of the ocular surface do not directly test this (5-7). The principal aim of this work was to correlate the wetting characteristics of the corneal epithelium in a hTERT cell line (HTCEpi cells) with the surface expression and spatial distribution of the cell associated mucins.

Although another immortalized hTERT corneal epithelium (HCLE), and a conjunctival epithelium (HCjE) cell lines have been tested for mucin expression (27), and exhibited the mucin repertoire characteristic of the native epithelium (albeit at lower mRNA levels), to our knowledge, the hTCEpi immortalized corneal epithelial cell line has not been previously characterized with respect to mucin expression (11). We observed a time-dependent increase in mucin expression during the first three days, and then a decrease thereupon (confirmed through mRNA and protein). Hori el al. analyzed the expression profile of HCjE during the stratification process, up to three days, and observed an increase of mucin expression, albeit with an independent pattern of regulation, similar to the first three days of our experiments (28). Furthermore, similar to our results they also observed low but detectable levels of MUC1 and MUC16 mRNA in unstratified cultures and no detectable expression of MUC4 (28). Further studies will indeed be required to validate our findings in vivo. In our experiments, the mRNA expression profiles for MUC1 and MUC16 corresponded to their protein expression profile. In contrast, for MUC4, mRNA expression peaked at day 3, but there was a monotonic increase in protein expression up to day 6, which may reflect a very low turnover of MUC4 in the cell cultures.

Once the expression profile of mucins was established, the surface properties of the cell cultures were characterized by the measurement of contact angles. The contact angle is a thermodynamic property (29). However, our observation of a very high contact angle hysteresis indicates a non-equilibrium state of the drops on the cellular surface and therefore prevents the measurement of a meaningful single surface energy (29,30). Nonetheless, this large contact angle hysteresis on cells subjected to the stratification process indicates the presence of "defects" on the surface, at which the drops are pinned, impeding the advancement and retraction of the drop and generating a difference in the advancing and the receding contact angles (30). The development of this contact angle hysteresis suggests the development of spatial surface heterogeneities with the most likely possibilities being the development of spatially discrete topographic features (31) or surface chemistry functionality (32) on the cell cultures. Furthermore, the hysteresis profile matches both the mucin expression and the surface heterogeneity of the cell cultures, pointing to the impact of mucins on this surface phenomenon.

To determine whether rugosity (amplitude of surface topographic features) contributed to the hysteresis of the contact angle, we imaged the culture surface using AFM (FIG. 8). Surface roughness does not change substantially once the cells are plated in stratification media. The RMS value of the surface significantly reduces between day 0 (in GM) and day 1 (in SM) and remains fairly stable up to day 6 (in SM). We noted significant flattening of superficial epithelial cells with stratification. The unstratified cells showed a cobblestone morphology, with tall and distinct cells resembling the morphology of basal corneal epithelial cells (33), while the stratified cultures showed a very flat surface consistent with the flattened, squamous apical epithelial surface cells (33). Development of surface topography contributes to the increase of contact angle hysteresis observed in our experiments; however, similar RMS values of cells in SM strongly suggest other factors as the source of the observed increase in hysteresis upon differentiation.

To elucidate the surface elements affecting the high contact angle hysteresis in stratified cells, we also tested the distribution of glycosylated proteins on the surface of the cell cultures by imaging with fluorescently-tagged Jacalin. Jacalin is a plant-based lectin, found in jackfruits, that binds to Gal/GalNAc and is considered a prime candidate to generically select O-glycans (34). Jacalin has been reported to bind intracellularly to the perinuclear region in HCLE cells (35). To minimize the internalization of the reporter dyes we designed an assay using streptavidin-coated Qdots that are not membrane permeable (36) and ensure the binding to the O-glycans decorating the cell surface. We observed major differences in the distribution of O-glycans on the cell surface between undifferentiated and stratified cells. Notably, a "mosaic" pattern was observed in stratified cell cultures. Such a pattern has been observed previously and correlated to normal eyes in vivo, while pathological patterns (such as a "starry sky pattern") correspond to dry eye patients (26,37), suggesting that the heterogeneity of the surface chemistry of the ocular surface may play an important role in dry eye syndrome. Considering that a high contact angle hysteresis is linked to the pinning of the contact line (32), this phenomenon may also influence the dewetting of the tear film by stabilizing the contact line between the ocular surface and the aqueous tear film, impeding the initiation and expansion of dry patches. Future experiments involving measurements obtained in vivo need to be performed to determine the influence of soluble biomolecules and lipids on contact angle hysteresis evidenced by the ocular surface.

In summary, we have developed a method to characterize biophysical surface properties on cell cultures measuring the contact angle and contact angle hysteresis with 2-liquids, ensuring the normal level of hydration of the cell surface and avoiding disruption of the chemical components of the cellular membrane. The high value of contact angle hysteresis in our cell cultures precluded us from obtaining meaningful values for surface energy. However, the same large contact angle hysteresis informs us about the development of surface functional heterogeneity of mucin expression and spatial distribution with differentiation of corneal epithelial cells. To our knowledge, this is the first report on contact angle hysteresis on the corneal epithelium. The magnitude of the contact angle hysteresis is related to a "retentive force" that stabilizes and pins drops in an inclined plane (38). This retentive force may play an important role in the stability/instability of liquid films on the ocular surface, and it could have a major implication on the development of dry eye syndromes. Differences in contact angle hysteresis are useful to diagnose the health of the ocular surface. Engineering the surface properties of the corneal and conjunctival epithelia allows for increasing the stability and retention of the tear film on the ocular surface.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A device to measure contact angle and contact angle hysteresis on a surface or layer of live/viable cells, the device comprising:
   i) a hollow outer cylinder comprised of a transparent material comprising a top end and a bottom end, the top end comprising an aperture of a diameter sufficient to allow passage of a syringe; the bottom end configured to form a liquid impermeable seal between an inner space of the cylinder and the surface of the eye of a mammal, the hollow outer cylinder containing a first fluid that is isotonic to the cells of the eye; and
   ii) a syringe comprising an inner cylinder and plunger, the syringe positioned along the center axis of the hollow outer cylinder, wherein the syringe contains a second fluid that is immiscible with the first fluid and comprises a higher density than the first fluid and the plunger dispenses the second fluid into the inner space of the hollow outer cylinder near the bottom end.

2. The device of claim 1, wherein the first fluid that is isotonic to the cells of the eye is transparent.

3. The device of claim 1, wherein the first fluid that is isotonic to the cells of the eye is colorless.

4. The device of claim 1, wherein the first fluid that is isotonic to the cells of the eye is selected from saline solution or artificial tears.

5. The device of claim 1, wherein the hollow outer cylinder is comprised of a material selected from the group consisting of glass, quartz or polymethylmethacrylate (PMMA).

6. The device of claim 1, wherein the hollow outer cylinder comprises an inner diameter in the range of from 10-15 mm.

7. The device of claim 1, wherein the bottom end of the hollow outer cylinder is configured to form a liquid impermeable seal between an inner space of the cylinder and the surface of the cornea of the mammal.

8. The device of claim 1, wherein the aperture is centered in the top end of the hollow outer cylinder.

9. The device of claim 1, wherein the syringe comprises an outer diameter in the range of from 5-10 mm.

10. The device of claim 1, wherein the syringe comprises a blunt end needle.

11. The device of claim 10, wherein the needle comprises a gauge in the range of 22-28 (OD 0.72-0.36 mm and ID 0.41-0.18 mm).

12. The device of claim 1, wherein the bottom end of the hollow outer cylinder comprises a cuff or ring or skirt comprised of a flexible and/or form-fitting material.

13. The device of claim 1, wherein the second fluid is selected from the group consisting of a perfluorocarbon and a silicon oil.

14. The device of claim 13, wherein the perfluorocarbon is selected from the group consisting of perfluorodecalin, perfluorooctane and tetradecafluorohexane.

15. A system comprising a device according to claim 1 and a camera positioned and focused to obtain images of the surface of the eye sealed within the hollow outer cylinder.

16. The system of claim 15, wherein the plunger of the syringe of the device is in communication with a regulator that depresses and retracts/pulls up the plunger in an automated and/or remotely controlled manner.

17. The system of claim 15, wherein the plunger of the syringe of the device is in communication with a microsyringe pump that depresses and retracts/pulls up the plunger in an automated and/or remotely controlled manner.

18. A method of determining the ability of a corneal surface of a subject to retain moisture, the method comprising:
   a) contacting the corneal surface of the subject with a device according to claim 1;
   b) dispensing one or more drops of the second fluid into the first fluid such that the drops of the second fluid contact the corneal surface of the subject;
   c) measuring at one or several points of contact (i) the advancing contact angle, and (ii) the receding contact angle of the drops of the second fluid in contact with the corneal surface;
   d) calculating the contact angle hysteresis of the combined measurements of the several points of contact, wherein a contact angle hysteresis value at or above a threshold value indicates a normal or sufficient ability of the corneal surface to retain moisture, and a contact angle hysteresis value below the threshold value indicates an abnormal or deficient ability of the corneal surface to retain moisture.

19. The method of claim 18, wherein the one or more drops comprise an average diameter of about 1-5 mm.

20. The method of claim 18, further comprising measuring the static contact angle.

21. The method of claim 18, further comprising moving the device to a second point of contact on the corneal surface and repeating steps b) to d).

22. The method of claim 18, wherein the measuring step is performed by obtaining a collection of digital images of the drops of the second fluid in contact with the corneal surface.

23. The method of claim 18, wherein the advancing contact angle values are measured at predetermined time increments while the contact point of the drop advances across the corneal surface.

24. The method of claim 18, wherein the receding contact angle values are measured at predetermined time increments while the contact point of the drop recedes across the corneal surface.

25. The method of claim 18, wherein the contact angle hysteresis value of the combined measurements of the several points of contact is calculated by applying the equation: $\cos\theta_{rec} - \cos\theta_{adv}$.

26. The method of claim 18, wherein the threshold value is in the range of about 0.6 to 1.0.

* * * * *